US009383373B2

(12) United States Patent
Green et al.

(10) Patent No.: US 9,383,373 B2
(45) Date of Patent: Jul. 5, 2016

(54) METHODS FOR DETECTING FUNGAL INFECTION

(75) Inventors: Bernard S. Green, Rechovot (IL); Inna Tzomik, Modiln (IL); Rina Arad-Yellin, Rechovot (IL)

(73) Assignee: Semorex Inc., Fanwood, NJ (US)

( * ) Notice: Subject to any disclaimer, the term of this patent is extended or adjusted under 35 U.S.C. 154(b) by 615 days.

(21) Appl. No.: 12/084,702

(22) PCT Filed: Nov. 15, 2006

(86) PCT No.: PCT/IL2006/001318
§ 371 (c)(1),
(2), (4) Date: May 8, 2008

(87) PCT Pub. No.: WO2007/057891
PCT Pub. Date: May 24, 2007

(65) Prior Publication Data
US 2009/0111129 A1    Apr. 30, 2009

Related U.S. Application Data

(60) Provisional application No. 60/736,814, filed on Nov. 15, 2005.

(51) Int. Cl.
G01N 33/569    (2006.01)
C07K 16/14     (2006.01)
C12P 21/00     (2006.01)
C07D 249/08    (2006.01)
C08F 122/38    (2006.01)
G01N 33/82     (2006.01)

(52) U.S. Cl.
CPC ..................................... *G01N 33/82* (2013.01)

(58) Field of Classification Search
CPC .... A61K 39/0002; G01N 33/82; G01N 33/92
See application file for complete search history.

(56) References Cited

U.S. PATENT DOCUMENTS 6,224,902 B1    5/2001    Alving et al.
7,087,395 B1    8/2006    Garrity et al.

FOREIGN PATENT DOCUMENTS

DE    19814815       10/1999
WO    WO 2007/057891  5/2007

OTHER PUBLICATIONS

Galina et al. (Journal of Organic Chemistry, 1966, vol. 31, pp. 2397-2398).*
Communication Pursuant to Article 94(3) EPC Dated Mar. 3, 2010 From the European Patent Office Re.: Application No. 06821559.9.
International Search Report and the Written Opinion Dated Jul. 7, 2008 From the International Searching Authority Re.: Application No. PCT/IL06/01318.
Response Dated Jun. 30, 2010 to Communication Pursuant to Article 94(3) EPC of Mar. 3, 2010 From the European Patent Office Re.: Application No. 06821559.9.
International Preliminary Report on Patentability Dated Jan. 22, 2009 From the International Bureau of WIPO Re.: Application No. PCT/IL2006/001318.
Walker-Caprioglio et al. "Antibodies to Nystatin Demonstrate Polyene Sterol Specificity and Allow Immunolabeling of Sterols in Saccharomyces Cerevisiae", Antimicrobial Agents and Chemotherapy, 33(12): 2092-2095, Dec. 1989.
Communication Pursuant to Article 94(3) EPC Dated Jan. 16, 2014 From the European Patent Office Re. Application No. 06821559.9.
Communication Pursuant to Article 94(3) EPC Dated Mar. 28, 2012 From the European Patent Office Re.: Application No. 06821559.9.
Tejada-Simon et al. "Production of Polyclonal Antibody Against Ergosterol Hemisuccinale Using Freund's and Titermax Adjuvants", Journal of Food Protection, XP009125825, 61(8): 1060-1063, Aug. 1, 1998.
Communication Pursuant to Article 94(3) EPC Dated Jun. 25, 2013 From the European Patent Office Re. Application No. 06821559.9.
Communication Pursuant to Article 94(3) EPC Dated Jun. 6, 2014 From the European Patent Office Re. Application No. 06821559.9.

* cited by examiner

Primary Examiner — Robert A Zeman

(57) ABSTRACT

Methods and kits which utilize a conjugate, preferably an adduct, of ergosterol for determining the presence or level of a broad spectrum of ergosterol-containing organisms (e.g., fungi) in various substrates are disclosed. These methods and kits can be used to accurately and efficiently diagnose a subject having a fungal infection, particularly invasive fungal infection, and to accurately and efficiently detect the presence of fungi and other ergosterol-containing organisms in other substrates. Antibodies and other compounds (e.g., molecularly imprinted polymers) that are capable of selectively binding to ergosterol or to an ergosterol-containing conjugate and methods of producing same are also disclosed.

8 Claims, 6 Drawing Sheets
(4 of 6 Drawing Sheet(s) Filed in Color)

METHODS FOR DETECTING FUNGAL INFECTION

RELATED APPLICATIONS

This Application is a National Phase of PCT Patent Application No. PCT/IL2006/001318 having International filing date of Nov. 15, 2006, which claims the benefit of U.S. Provisional Patent Application No. 60/736,814 filed on Nov. 15, 2005. The contents of the above Applications are all incorporated herein by reference.

FIELD AND BACKGROUND OF THE INVENTION

The present invention relates to novel methods and kits for detecting fungal infections, particularly invasive fungal infections, which are based on ergosterol as a biomarker for the presence of fungi. The methods and kits can be utilized for medical diagnosis of a broad spectrum of fungal infections, as well as for detecting fungi in the environment, in food products and in other substances.

The incidence of fungal infections and mycoses has increased significantly in the past two decades, mainly due to the growing number of individuals who have reduced immunological function (immuno-compromised patients), such as cancer patients, patients who have undergone organ transplantation, patients with AIDS, patients undergoing hemodialysis, critically ill patients, patients after major surgery, patients with catheters, patients suffering from severe trauma or burns, patients having debilitative metabolic illnesses such as diabetes mellitus, persons whose blood is exposed to environmental microbes such as individuals having indwelling intravenous tubes, and even in some elderly individuals. Fungal infections are often also attributed to the frequent use of cytotoxic and/or antibacterial drugs, which alter the normal bacterial flora.

Fungi include moulds, yeasts and higher fungi. All fungi are eukaryotic and have sterols but not peptidoglycan in their cell membrane. They are chemoheterotrophs (requiring organic nutrition) and most are aerobic. Many fungi are also saprophytes (living off dead organic matter) in soil and water and acquire their food by absorption. Characteristically fungi also produce sexual and asexual spores. There are over 100,000 species recognized, with 100 infectious members for humans.

Human fungal infections are uncommon in generally healthy persons, being confined to conditions such as Candidiasis (thrush) and dermatophyte skin infections such as athlete's foot. Nevertheless, yeast and other fungi infections are one of the human ailments which still present a formidable challenge to modern medicine. In an immuno-compromised host, a variety of normally mild or nonpathogenic fungi can cause potentially fatal infections. Furthermore, the relative ease with which human can now travel around the world provides the means for unusual fungal infections to be imported from place to place. Therefore, wild and resistant strains of fungi are considered to be one of the most threatening and frequent cause of death mainly in hospitalized persons and immuno-compromised patients.

Invasive fungal infection (IFI) is a serious and potentially life threatening disease that affects a growing number of patients. The projected average incidence of systemic fungal infections in the United States is 306 per million, with Candidiasis accounting for 75% of the reported cases [see, for example, Wilson et al. Value in Health, 5, 26-34, 2002].

Mortality rates in cancer patients who develop systemic fungal infections are very high. It has been observed that fungi are the most common cause of nonbacterial infection in patients with leukemia and lymphoma, with Candida species and Aspergillus being the most common fungal species in cancer patients. These two infections are estimated to have a combined mortality of 20% (Lopez-Berestein et al., Cancer Drug Delivery, 1:37-42, 1983). In other cases, fungal or fungus-like infections, usually introduced into the lungs through the air, are commonplace among large numbers of persons due to environmental exposures.

Certain other organisms that have parasitic properties, such as leishmaniasis, can mimic many of the disease-causing properties, behaviors, and pathologies of fungal infections.

Accurate data regarding the incidence of systemic mycoses and associated mortality are difficult to obtain because reporting requirements vary; many fungal-related deaths are not reported as such because they are undiagnosed, misdiagnosed, or not specified as cause of death. Nevertheless, many indications suggest that the incidence of fungal infections and their attributable mortality are rising. This reflects the increasing number of susceptible hosts due to factors such as the HIV epidemic, advances in organ transplantation and cancer chemotherapy, and the increasing use of invasive procedures for treatment, monitoring, and life support. Estimates are that among the 35 million patients admitted to hospitals in the United States each year, at least 2.5 million will develop nosocomial infections. Almost 250,000 of these will be bloodstream infections, which contribute significantly to excess length and cost of hospital stays and patient mortality. The attributable mortality from bloodstream infections averages 26% but varies according to the specific organism involved.

Of all the pathogens isolated, Candida had the highest attributable mortality rate (40%) [Edmond et al. Clin. Infect. Dis. 29, 239-244, 1999]. Data collected by the NNIS (National Nosocomial Infections Surveillance System) showed that between 1980 and 1989 the incidence of nosocomial candidemia increased by almost 500% in large teaching hospitals and by 219% and 370% in small teaching hospitals and large non-teaching hospitals, respectively [Banerjee et al. Am. J. Med. 91 (suppl. 3B), 86S-89S, 1991]. For an overview of invasive Candidiasis see, for example, http://www.doctorfungus.org/mycoses/human/candida/InvasiveOverview.htm.

Invasive fungal infections therefore pose a major challenge for the management of immuno-compromised and other patients. Currently, mortality rates are high and effective treatment is hampered by the lack of reliable early diagnosis. Since the clinical symptoms of IFI are non-specific, with fever often being the only symptom at the outset, there is a widely recognized need for diagnosis methods that would allow early diagnosis of IFI and thereby would improve the medical outcome and survival of these patients.

Current diagnoses of fungal infections include conventional microbiological, histological and radiological techniques. These techniques, however, are often insufficiently sensitive and have a limited impact on clinical decision-making [Pasqualotto and Denning Europ. Oncology Rev. 1-11, 2005].

The current "gold standard" diagnostic method for fungal infection remains culturing of affected tissue or blood. These cultures are inadequate as they very often fail to grow. It is commonly accepted that blood cultures are positive in less than 50% of patients with autopsy-proven systemic fungal infection [Rodriguez et al. Adv. Pharmacol. 37, 349-400 (1997)]. A recent large retrospective study even suggests that 75% of IFI cases were not found antemortem [Chamilos et al. *Haematologica*, 91, 986-989 (2006)].

In an attempt to answer the needs for the diagnosis of this elusive group of diseases, various studies have focused on developing new tests. These include, for example, serologic tests and direct blood tests.

Serologic tests (i.e., the detection of specific antibodies to the disease) are difficult to interpret, a feature that often leads to false positive or negative diagnoses. In many cases, since the hosts are immuno-compromised to begin with, serological tests yield no results whatsoever.

Direct blood tests are currently expected to challenge the culturing method and eventually become the gold standard. While still limited in many ways, these tests detect specific antigens, DNA segments, or enzymes present in the blood during the early stages of IFI. Although promising, these tests are presently limited by insufficient specificity, are difficult to deploy since they require expensive infrastructure or laborious preparations, are sometimes difficult to interpret, have cross-reactivity in various clinical settings with common therapies, and are in many cases, prohibitively expensive.

A characteristic commonly shared by organisms that cause all of the above diseases is the presence of ergosterol as the predominant or sole sterol in place of cholesterol.

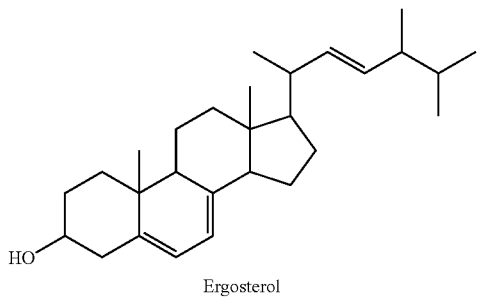 [SMILES: CC(C)C(C)/C=C/C(C)C1CCC2C3=CC=C4CC(O)CCC4(C)C3CCC21C]
Ergosterol

Ergosterol, a steroid and a precursor to Vitamin D2, is a major component of fungal cell membranes, serving the same function that cholesterol serves in animal cells. Ergosterol is either absent or a minor component of higher plants. The presence of ergosterol in fungal cell membranes coupled with its absence in animal cell membranes makes it a uniquely useful target for fungal diagnostics and antifungal drugs.

In a study of the relationship between viable mould count, ergosterol content and ochratoxin A formation, it was shown that ergosterol assay is useful in the detection of fungus [Saxena et al., *Int. J. Food Microbio* 71, 29-34 (2001)]. Measurement of ergosterol content was developed as a new method for susceptibility testing of drugs [Arthington-Skaggs et al., *Antimicrob. Agents Chemother.* 44, 2081-5 (2000)]. Ergosterol determination has also recently been used for determining airborne fungi [Robine et al. *J. Microbiol. Meth.* 63, 185-192 (2005)], and for determining fungi in environmental samples [Volker, et al. *J. Chem. Ed.* 77, 1621-3 (2000)].

Hitherto, ergosterol has never been used as a biomarker for systemic fungal infection, probably because appropriate isolation and analytical methods for determining ergosterol levels in clinical samples are not available up to now [Parsi and Gorecki *J. Chromatogr. A* 1130(1), 145-50 (2006)]. Current methods for ergosterol detection are based on HPLC, mass spectrometry and other analytical instrumentation, which are usually not available in clinical laboratories, are time-consuming and require skilled personnel.

While clinical laboratories often use immunoassay methodologies for diagnosis, these methodologies are ineffective for detecting ergosterol. Ergosterol, as other sterols, is a small, lypophilic molecule, which is typically present in inner membranes. It is well-known in the art that producing effective, specific and sensitive antibodies for such substances, which could be utilized in in vitro diagnoses, is highly difficult and often impossible. Ergosterol is therefore considered as a non-immunogenic molecule [Tejada-Simon and Pestka *J. Food Protection* 61, 1060-3 (1998)].

One way to overcome the non-immunogenicity of sterols is by conjugation to carrier molecules. However, it is well-known that antibodies generated against sterol compounds conjugated to carrier molecules often cross-react to varying degrees with sterols having similar structures. The basis for cross-reactivity of such antibodies lies in the fact that all of the target compounds against which the antibodies are directed have a similar cyclopentanoperhydrophenanthrine-like multiple ring sterol structure.

U.S. Patent Application Publication No. 20020018808 teaches liposomal or other delivery compositions that contain ergosterol or ergosterol derivatives, and methods of using same. These compositions are useful for immunizing humans and animals against fungal infections and for the treatment and prevention of fungal infection. U.S. Patent Application No. 20020018808 further teaches diagnostic assays and kits for determining whether a human or animal has a fungal infection by measuring antibodies to ergosterol, whereby these assays and kits utilize plates having ergosterol or anti-ergosterol antibodies bound thereto.

While U.S. Patent Application No. 20020018808 suggests a synthetic pathway for preparing N-[(3β,22E)-ergosta-5,7,22-trien-3-(succinylamido)]dimyristoyl-phosphatidyl ethanolamine, a phosphatidyl ergosterol, to be encapsulated within liposome, so as to serve as a vaccine composition, the use of such ergosterol-containing liposomes and the efficient production of antibodies against ergosterol upon administering these liposomes are not described.

1,2,4-Triazoline-3,5-dione (TAD) and derivatives thereof are well-known dienophiles which have been widely utilized and studied in the Diels-Alder reaction with 1,3-diene-containing compounds, including substances in biological systems. For example, a 4-N-pentafluorobenzyl-1,2,4-triazoline-3,5-dione was shown to react with an analog of vitamin D3 and it was suggested that this approach could be used for detecting vitamin D2, vitamin D3 and other drugs or biological substances containing a 1,3-diene moiety [see, for example, Wang, et al., *Anal. Biochem.* 243, 28-40 (1996)]. Thus, for example, a triazolinedione derivative was used to simultaneously determine vitamin D2 and vitamin D3 in plasma [Higashi et al., *Biol. Pharm. Bull.* 24, 738-743 (2001)].

By including a 1,3-diene moiety, ergosterol has been used in various studies concerning Diels-Alder reactions of sterols and various dienophiles (see, for example, U.S. Pat. No. 6,399,796). Thus, conjugates of ergosterol and triazolinedione derivatives have been reported. For example, an adduct of 4-phenyl-1,2,4-triazoline-3,5-dione and ergosterol was prepared [Gilani and Triggle, *J. Org. Chem.* 31, 2397 (1966)]. These conjugates, however, have never been utilized in diagnostic methods for detecting fungal infections by measuring the level of ergosterol.

As discussed hereinabove, despite recent advances in treatment, mortality rates of invasive fungal infections remain unacceptably high, particularly with regard to the two most common pathogen groups, *Candida* and *Aspergillus*. Fast, accurate diagnosis remains a key obstacle in the treatment of invasive as well as other fugal infections.

There is thus a widely recognized need for, and it would be highly advantageous to have, an ergosterol-based biomarker for the accurate, fast and specific detection of fungi and methods and kits utilizing same, devoid of the above limitations.

SUMMARY OF THE INVENTION

The present inventors have now uncovered that a compound that is capable of selectively forming a conjugate with ergosterol can be efficiently utilized for detecting ergosterol and thus for detecting an ergosterol-containing organism in a substrate. The present inventors have therefore devised methods and kits that utilized the formation of such a conjugate as an efficient tool for detecting fungal infections and/or fungal presence in various substances. These methods and kits are far superior to the presently known configurations since they provide fast, sensitive and cost-effective detection of ergosterol-containing compounds. Utilizing such a conjugate, the present inventors have further devised recognizing substances that selectively bind the conjugate or ergosterol per se and processes of producing or preparing same.

According to one aspect of the present invention there is provided a method of determining a presence and/or a level of an ergosterol-containing organism in a substrate, the method comprising: contacting at least a portion of the substrate with a compound capable of selectively forming a conjugate with ergosterol; and determining a presence and/or a level of the conjugate, the presence and/or level of the conjugate being indicative for the presence and/or level of an ergosterol-containing organism in the substrate.

According to another aspect of the present invention there is provided a use of a compound capable of selectively forming a conjugate with ergosterol for determining a presence and/or a level of an ergosterol-containing organism in a substrate, wherein a presence and/or a level of the conjugate is indicative for the presence and/or level of an ergosterol-containing organism in the substrate.

According to further features in preferred embodiments of the invention described below, the compound comprises a detectable moiety.

According to still further features in the described preferred embodiments the determining is effected by an analytical technique selected from the group consisting of a chromatographic assay, a spectroscopic assay, a spectrophotometric assay, a radioactivity assay, an electrochemical assay and an immunoassay.

According to still further features in the described preferred embodiments the analytical technique is selected from the group consisting of high-performance liquid chromatography (HPLC), electron spin spectroscopy, a phosphorescence assay, a fluorescence assay, a chromogenic assay, a luminescence assay, a quartz crystal microbalance assay and an enzymatic assay.

According to still further features in the described preferred embodiments the method further comprises subsequent to, or concomitant with, contacting the compound with the substrate, contacting the substrate and the compound with a recognizing substance, the recognizing being capable of selectively binding the ergosterol and/or the conjugate to thereby obtain a complex of the recognizing substance and the conjugate, wherein determining a presence and/or a level of the complex is indicative of the presence and/or level of the conjugate.

According to still further features in the described preferred embodiments determining the presence and/or level of the conjugate is effected in the presence of a recognizing substance, aid recognizing being capable of selectively binding the ergosterol and/or the conjugate to thereby obtain a complex of the recognizing substance and the conjugate, wherein determining a presence and/or a level of the complex is indicative of the presence and/or level of the conjugate.

According to still further features in the described preferred embodiments the recognizing substance comprises a detectable moiety.

According to still further features in the described preferred embodiments the recognizing substance is a quartz crystal microbalance plate having the compound attached thereto.

According to still further features in the described preferred embodiments the recognizing substance is an antibody capable of selectively binding the ergosterol and/or the conjugate.

According to still further features in the described preferred embodiments the antibody is produced by inducing an immunogenic response to the conjugate.

According to still further features in the described preferred embodiments the recognizing substance is selected from the group consisting of a molecularly imprinted polymer (MIP), a cavitand, a clathrate, a cryptand, a cyclodextrin, a calixarene, a cucurbituril, a porphyrin, a crown ether and a triazine.

According to still further features in the described preferred embodiments the recognizing substance is a molecularly imprinted polymer.

According to still further features in the described preferred embodiments the method described herein comprises isolating a sterol-containing portion of the substrate; contacting the sterol-containing portion with the compound; and subjecting the sterol-containing portion and the compound to a high-performance liquid chromatography (HPLC) assay, to thereby determine the presence and/or level of the conjugate, thereby determining the presence and/or level of an ergosterol-containing organism in the substrate.

According to still further features in the described preferred embodiments the method described herein comprises isolating a sterol-containing portion of the substrate; contacting the sterol-containing portion with the compound; contacting the sterol-containing portion and the compound with an antibody capable of selectively binding the conjugate to thereby obtain a complex of the antibody and the conjugate; and determining a presence and/or level of the complex, the presence and/or level of the complex being indicative of the presence and/or level of the conjugate, thereby determining the presence and/or level of an ergosterol-containing organism in the substrate.

According to still further features in the described preferred embodiments the compound comprises a detectable moiety.

According to still further features in the described preferred embodiments the antibody comprises a detectable moiety.

According to still further features in the described preferred embodiments the method described herein comprises isolating a sterol-containing portion of the substrate; contacting the sterol-containing portion with the compound; and contacting the sterol-containing portion and the compound with a molecularly imprinted polymer capable of selectively binding the ergosterol and/or the conjugate to thereby obtain a complex of the molecularly imprinted polymer and the conjugate; and determining a presence and/or a level of the complex, the presence and/or level of the complex being indicative of the presence and/or level of the conjugate, thereby determining the presence and/or level of an ergosterol-containing organism in the substrate.

According to still further features in the described preferred embodiments the molecularly imprinted polymer comprises a detectable moiety.

According to still further features in the described preferred embodiments the detectable moiety forms a part of a detectable conjugate of the compound and ergosterol, the detectable conjugate being released from the MIP upon obtaining the complex of the MIP and the conjugate.

According to still further features in the described preferred embodiments the method described herein comprises isolating a sterol-containing portion of the substrate; and contacting the sterol-containing portion with a molecularly imprinted polymer capable of selectively binding the ergosterol to thereby obtain a complex of the recognizing substance and the ergosterol, wherein determining a presence and/or level of the complex is indicative of a presence and/or level of the conjugate, the molecularly imprinted polymer comprises a moiety capable of forming the conjugate.

According to another aspect of the present invention there is provided a kit for determining a presence and/or a level of an ergosterol-containing organism in a substrate, the kit comprising: a compound capable of forming a conjugate with ergosterol.

The kit can further comprise a detecting unit for determining a presence and/or a level of the conjugate, the presence and/or level of the conjugate being indicative of the presence and/or level of an ergosterol-containing organism.

The kit can further comprise a solid support.

The kit can further comprise a recognizing substance capable of selectively binding the ergosterol and/or the conjugate to thereby obtain a complex of the recognizing substance and the conjugate, wherein determining a presence and/or a level of the complex is indicative of a presence and/or level of the conjugate.

According to further features in preferred embodiments of the invention described below, the recognizing substance is a quartz crystal microbalance plate having the compound attached thereto.

According to still further features in the described preferred embodiments the recognizing substance is an antibody capable of selectively binding ergosterol or the conjugate.

According to still further features in the described preferred embodiments the recognizing substance is selected from the group consisting of a molecularly imprinted polymer (MIP), a cavitand, a clathrate, a cryptand, a cyclodextrin, a calixarene, a cucurbituril, a porphyrin, a crown ether and a triazine.

According to still further features in the described preferred embodiments the recognizing substance is a molecularly imprinted polymer capable of selectively binding ergosterol and/or the conjugate.

According to further features in preferred embodiments of the invention described below, in any of the methods, uses and kits described herein the compound capable of forming a conjugate with ergosterol is a dienophile and the conjugate comprises an adduct of ergosterol and the dienophile.

According to still further features in the described preferred embodiments the dienophile has a general formula:

$$R1-X=Y-R2$$

wherein:
X is N or CR3;
Y is N or CR4;

R3 and R4 are each independently selected from the group consisting of hydrogen, alkyl, cycloalkyl or, alternatively, R3 and R4 together form a bond; and R1 and R2 are each independently selected from the group consisting of hydrogen, alkyl, cycloalkyl, halide, hydroxy, amine, thiol, aryl and an electron withdrawing group, or, alternatively, R1 and R2 together form a bridging moiety, provided that at least one of R1 and R2 is an electron withdrawing group or that the bridging moiety comprises at least one electron withdrawing group.

According to still further features in the described preferred embodiments the dienophile is selected from the group consisting of a 2,3-dihydrophthalazine-1,4-dione and a [1,2,4]-triazole-3,5-dione (TAD).

According to further features in preferred embodiments of the invention described below, in any of the methods, uses and kits described herein the ergosterol-containing organism is a fungus.

According to still further features in the described preferred embodiments the substrate is a bodily substrate selected from the group consisting of an organ, a tissue and a cell.

According to further features in preferred embodiments of the invention described below, any of the methods, uses and kits described herein is for detecting a fungal infection in a subject comprising the bodily substrate.

According to further features in preferred embodiments of the invention described below, in any of the methods, uses and kits described herein the substrate is a blood sample.

Alternatively, the substrate is selected from the group consisting of a construction, a storage container, a soil, an agricultural crop, a horticultural crop, an agricultural product, a food product, a cosmetic product, a paint, a lumber and a building material.

According to yet another aspect of the present invention there is provided an antibody comprising an antigen recognition domain capable of specifically binding to ergosterol.

According to further features in preferred embodiments of the invention described below, the ergosterol forms a part of a conjugate, the conjugate further comprising a compound covalently attached to ergosterol.

According to further features in preferred embodiments of the invention described below, the conjugate is a Diels-Alder adduct of the ergosterol.

According to still another aspect of the present invention there is provided a process of preparing the antibody described herein, the process comprising inducing an immunogenic response to a conjugate of ergosterol and a compound being covalently attached thereto, to thereby produce the antibody; and collecting the antibody. The conjugate is preferably a Diels-Alder adduct of the ergosterol.

According to an additional aspect of the present invention there is provided a compound capable of selectively binding an ergosterol.

According to further features in preferred embodiments of the invention described below, such a compound comprises a substance having a structural affinity to ergosterol and at least one functional group capable of forming an interaction with ergosterol.

According to still further features in the described preferred embodiments the functional group is capable of forming a covalent interaction with ergosterol.

According to still further features in the described preferred embodiments the functional group comprises a dienophile.

According to still an additional aspect of the present invention there is provided a compound capable of selectively binding an ergosterol-containing conjugate.

According to further features in preferred embodiments of the invention described below, such a compound comprises a substance having a structural affinity to the conjugate and at least one functional group capable of forming an interaction with the conjugate.

According to still further features in the described preferred embodiments the conjugate comprises ergosterol and a dienophile being covalently linked therebetween.

According to still further features in the described preferred embodiments the substance is a molecularly imprinted polymer.

According to a further aspect of the present invention there is provided a process of preparing an antibody which comprises an antigen recognition domain capable of specifically binding a substance, the process comprises inducing an immunogenic response to an adduct of the substance, to thereby produce the antibody; and isolating the antibody.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

As used herein, the singular form "a", "an" and "the" include plural references unless the context clearly dictates otherwise. For example, the term "a protein" or "at least one protein" may include a plurality of proteins, including mixtures thereof.

As used herein the term "about" refers to ±10%.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein throughout, the term "comprising" means that other steps and ingredients that do not affect the final result can be added. This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

The term "method" or "process" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1A:
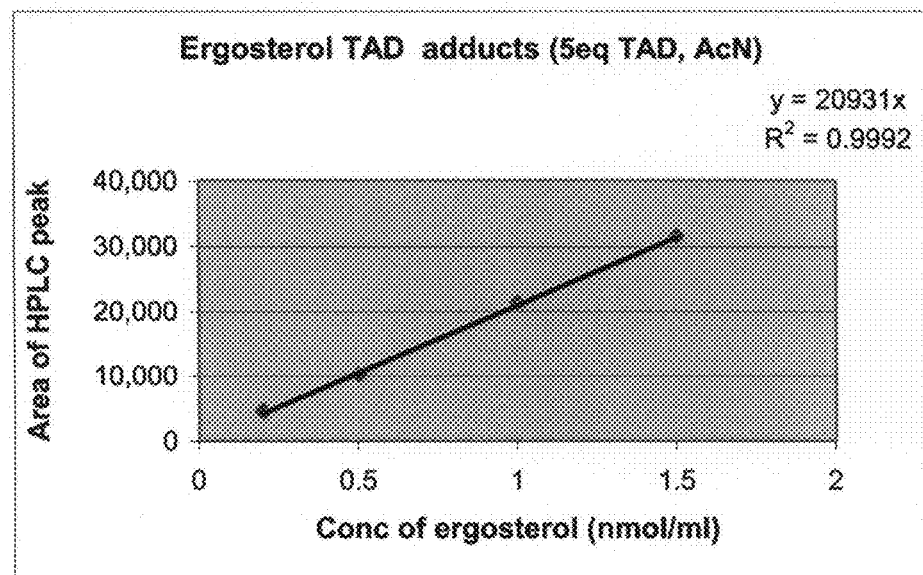
Figure 1B:
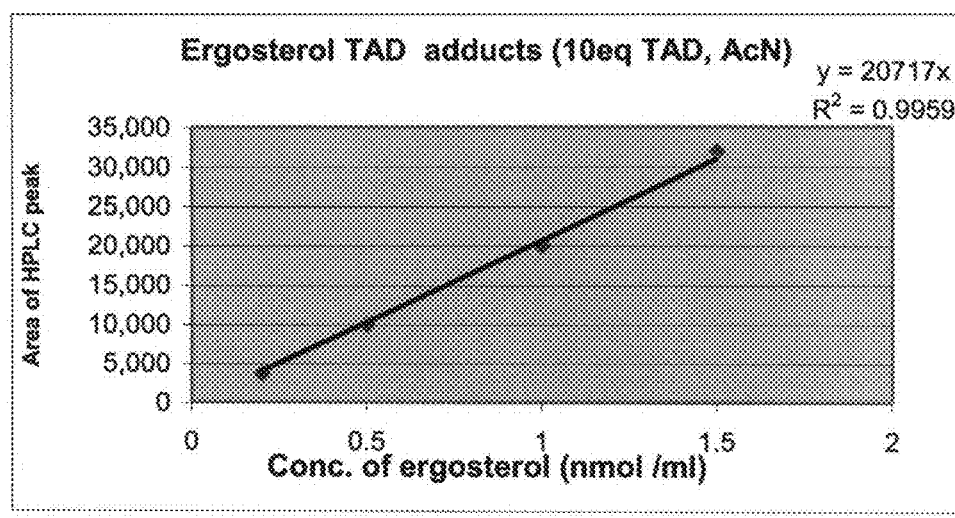
Figure 2:
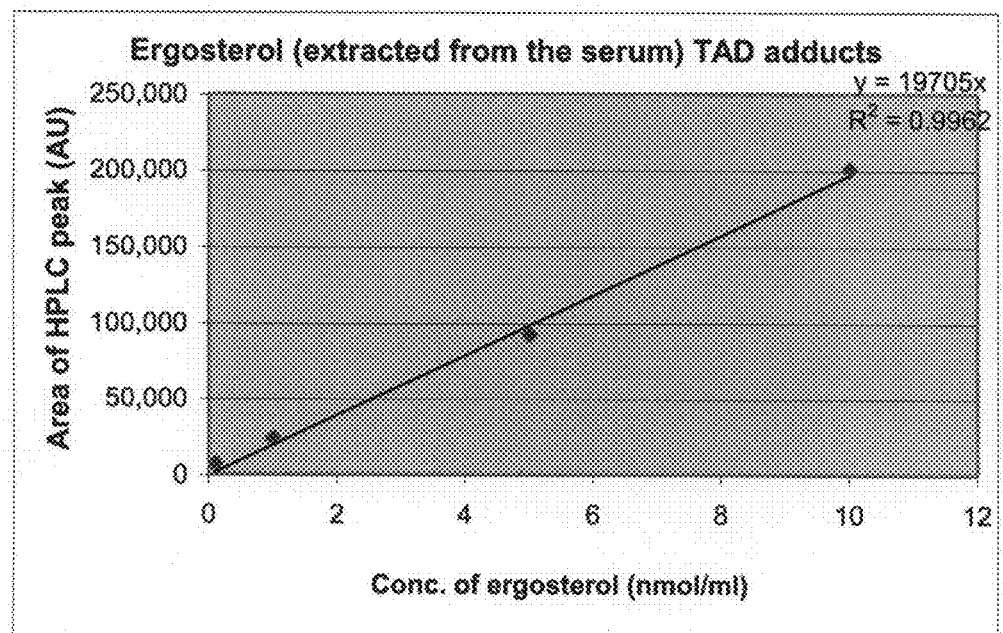
Figure 3A:
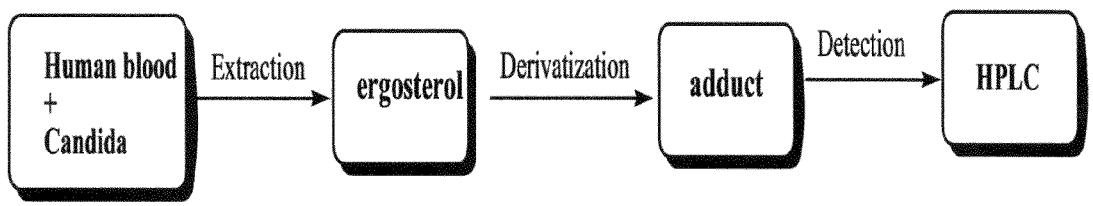
Figure 3B:
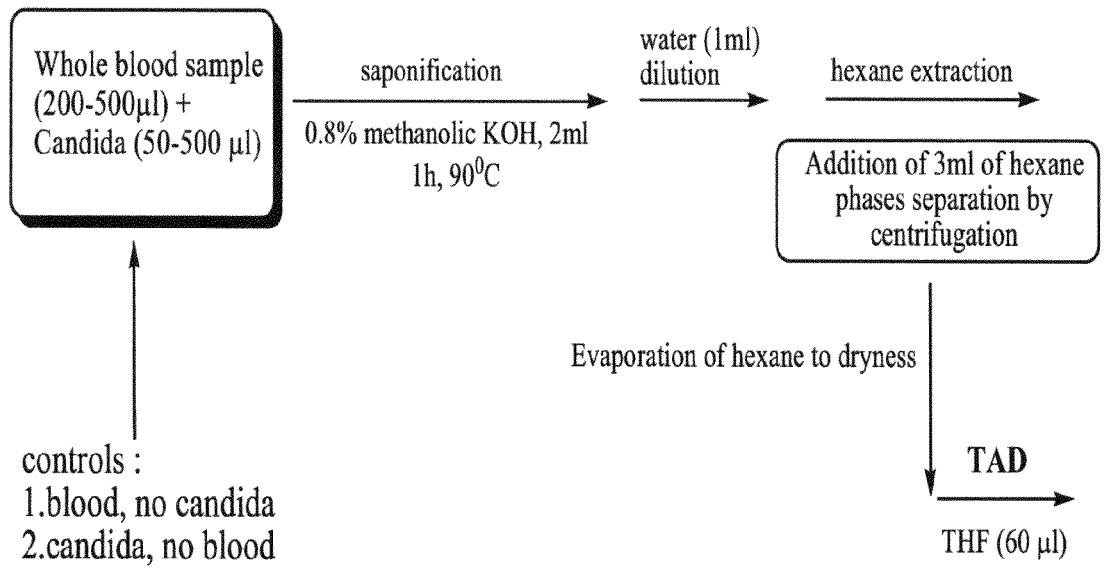
Figure 4A:
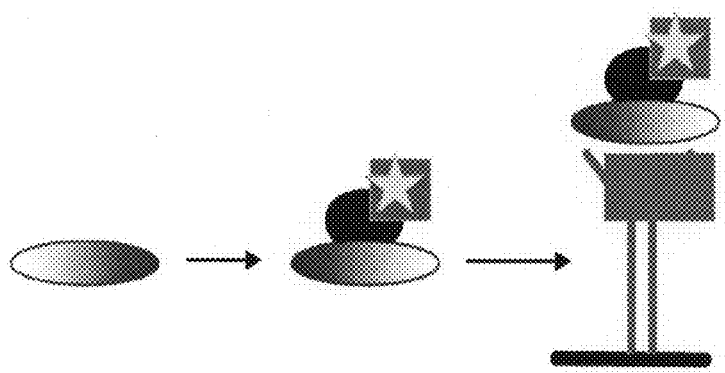
Figure 4B:
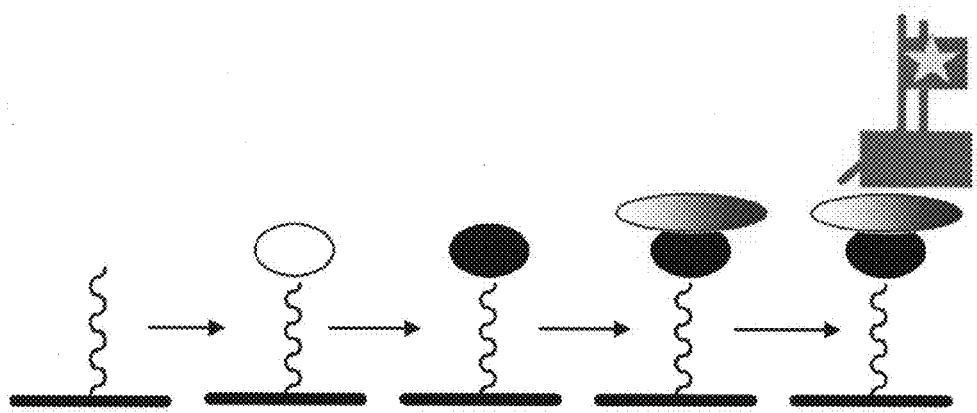
Figure 4C:
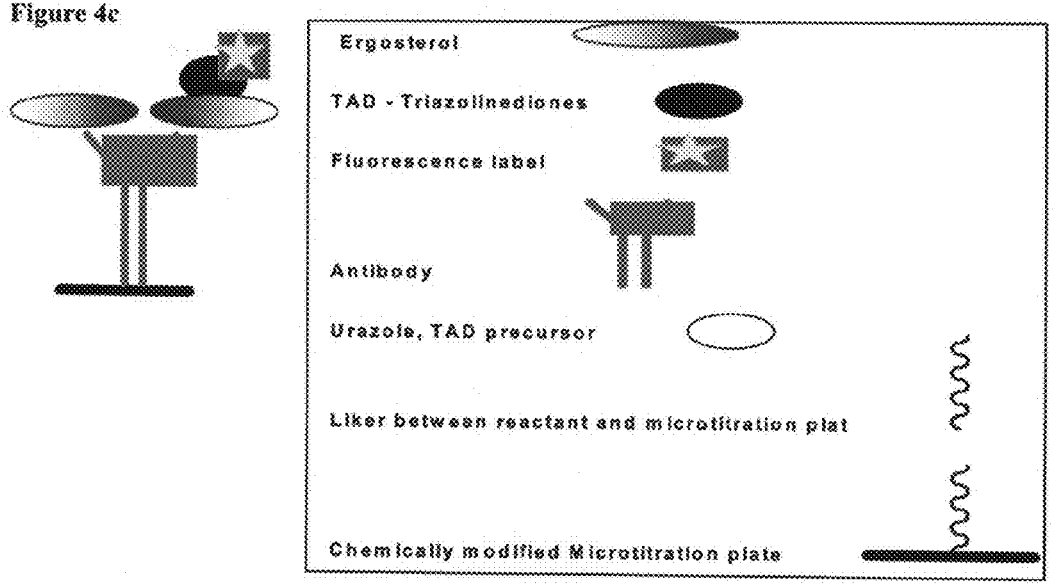
Figure 5:
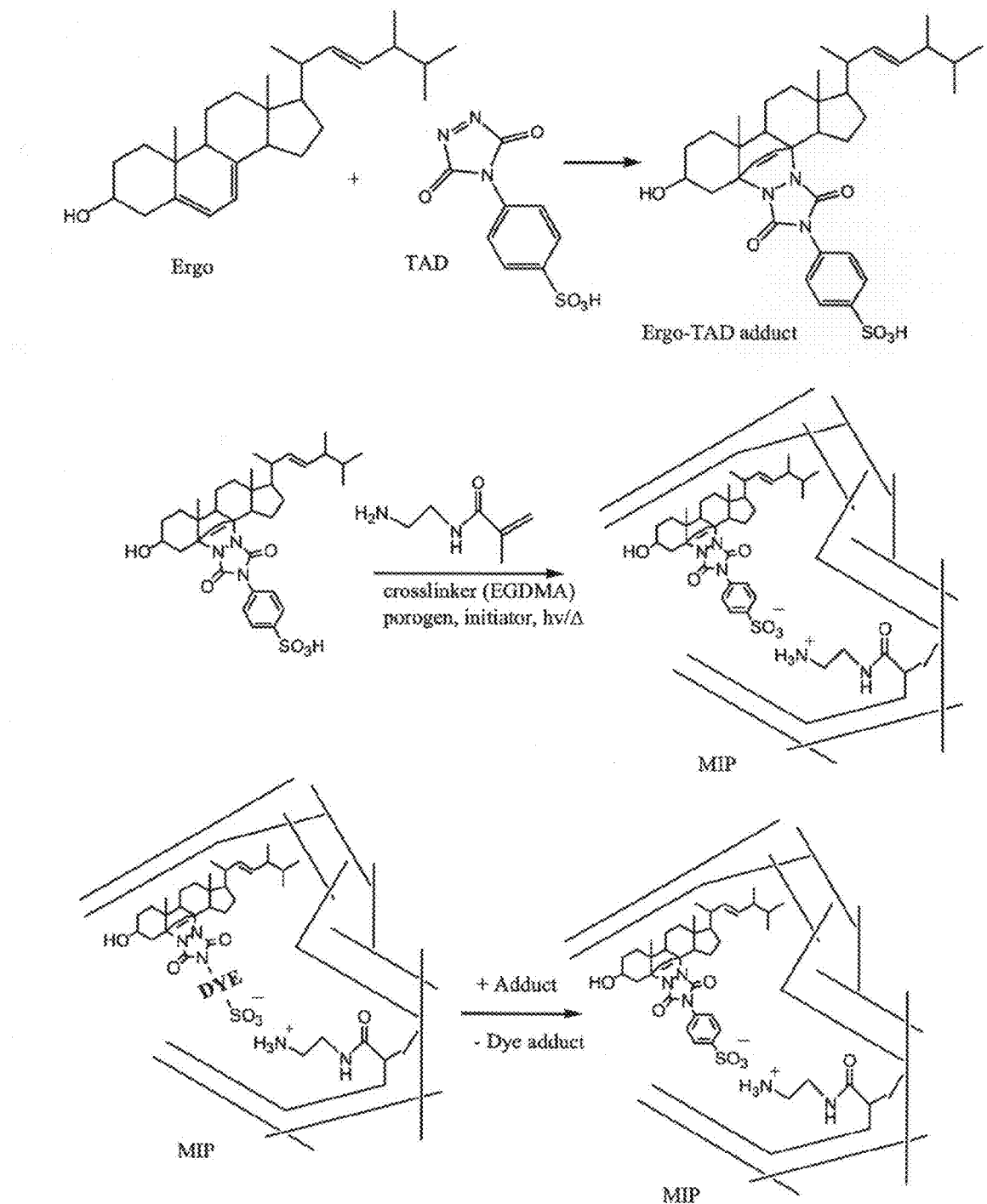
Figure 6A:
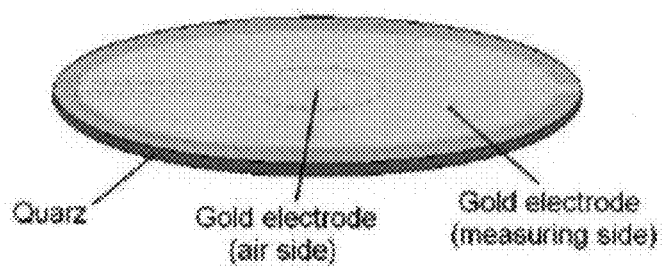
Figure 6B:
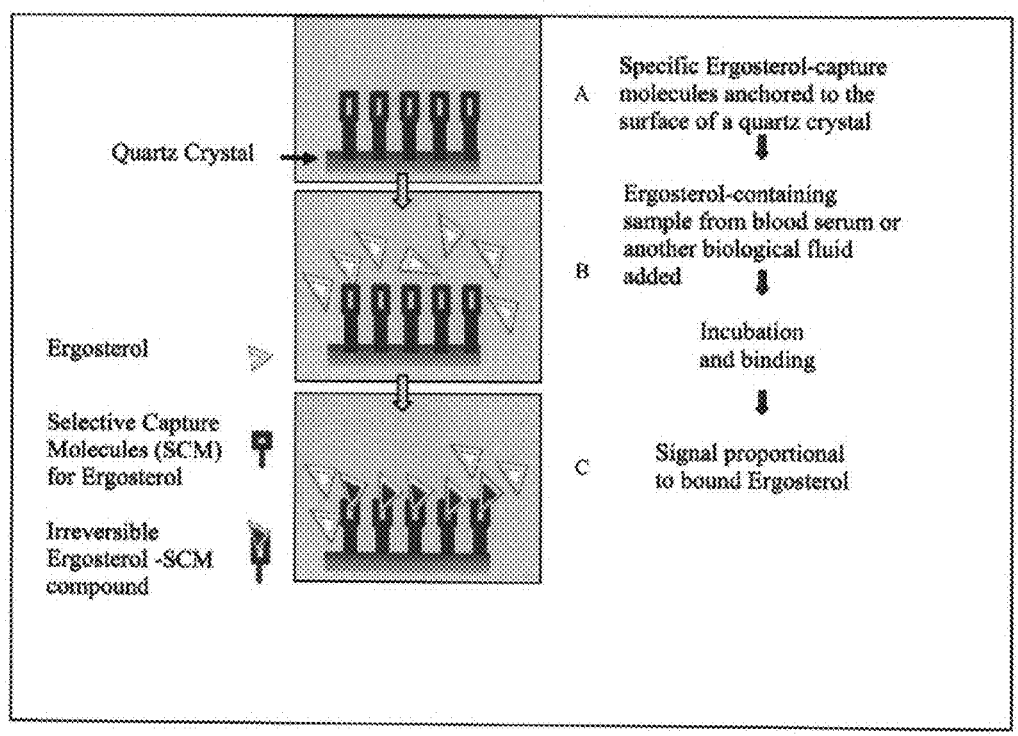

FIGS. 1a-b present graphs demonstrating the linearity in the spectrophotometric (UV) response obtained for increasing concentrations of an ergosterol-pyrenyl propyl TAD adduct (Compound 4) prepared by reacting increasing concentrations of ergosterol with 5 equivalents of pyrenyl propyl TAD (FIG. 1a) and 10 equivalents of pyrenyl propyl TAD (FIG. 1b);

FIG. 2 presents an exemplary graph demonstrating the linearity in the fluorescence response obtained in a representative experiment in which a serum sample was treated with increasing concentrations of ergosterol, the ergosterol was extracted and the extract was reacted with 10 equivalents of pyrenyl propyl TAD adduct (Compound 3), to obtain the ergosterol-TAD adduct Compound 4;

FIGS. 3a-b present flow charts describing en exemplary process according to the present embodiments for determining the level of ergosterol in whole blood samples spiked with *Candida Allbicans*, wherein FIG. 3a generally presents the process and FIG. 3b presents the procedures included within the extraction and derivatization stages of the process;

FIGS. 4a-c schematically illustrate exemplary assay principles for detecting ergosterol in a tested sample, which utilize an adduct of ergosterol and labeled or non-labeled TAD and a labeled or non-labeled antibody specific to ergosterol or to its TAD adduct, as detailed hereinafter;

FIG. 5 schematically illustrates a formation of a MIP that selectively binds an ergosterol-TAD adduct, according to preferred embodiments of the present invention (ergosterol is abbreviated as Ergo), and an exemplary assay principle for utilizing such a MIP for detecting and measuring the amount of ergosterol-TAD adduct (and thereby the amount of ergosterol) present in a sample (as the amount of ergosterol-TAD increases, the amount of dye released from the MIP increases);

FIGS. 6a-b present a schematic view of a Quartz Micro Balance detector (FIG. 6a) and a schematic view of a QCM sensor designed to selectively bind ergosterol, which has a TAD derivative attached thereto, wherein upon contacting the QCM with an ergosterol-containing sample, the ergosterol binds irreversibly to the QCM and a change in the crystal resonance is observed.

DESCRIPTION OF THE PREFERRED EMBODIMENTS

The present invention is of methods and kits which utilize a conjugate, preferably an adduct, of ergosterol for determining the presence or level of a broad spectrum of ergosterol-containing organisms (e.g., fungi) in various substrates. Specifically, the methods and kits of the present embodiments can be used to accurately and efficiently diagnose a subject having a fungal infection, particularly invasive fungal infection, and to accurately and efficiently detect the presence of fungi and other ergosterol-containing organisms in other substrates. The present invention is further of antibodies and other compounds (e.g., molecularly imprinted polymers) that are capable of selectively binding to ergosterol or to an ergosterol-containing conjugate and of methods of producing same.

The principles and operation of the present embodiments may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As discussed hereinabove, the increasing occurrence of invasive fungal infections and the attributable mortality rates have prompted researchers to look for improved diagnostic methods that would allow an early detection of the disease. These methods, however, are still limited by high cost, relatively low accuracy, insufficient specificity, and are often time consuming, require expensive infrastructure or laborious preparations and/or are prohibitively expensive.

In a search for a novel method for detecting fungi, the present inventors have devised a new methodology, which is based on the prevalent presence of ergosterol in fungi, as well as in other microorganisms, and its absence in higher organisms. The presence inventors have thus envisioned that forming a detectable conjugate that comprises ergosterol and a detectable compound covalently linked thereto and further designing such a conjugate that is readily detected by fast, accurate and convenient detection methods, would provide an efficient method for determining, both qualitatively and quantitatively, the presence of fungi and other ergosterol-containing organisms.

As further discussed and presented hereinabove, ergosterol is a 5,7-diene sterol. As a sterol, ergosterol fails to induce an immunogenic response due to its nature as a lipophilic small molecule and hence common immunoassays, often utilized in clinical laboratories and in portable detection kits, cannot be performed for detecting ergosterol.

The present inventors have envisioned that in order to produce a selective conjugate of ergosterol that would allow a specific detection thereof, the diene moiety of ergosterol should be used to form the conjugate. Particularly, the present inventors have envisioned that an efficient and selective conjugation could be effected via the well-known Diels-Alder addition reaction, by reacting the ergosterol with a dienophile, to thereby produce an adduct.

The use of such as adduct is highly advantageous since it allows fast and quantitative, and often selective, reaction with ergosterol, thus rendering the detection of ergosterol highly efficient. In addition, the formation of such an adduct via the Diels-Alder chemistry, allows to use a dienophile that have a myriad of detectable moieties attached thereto, without interfering with the reaction progress, as long as these moieties do not affect the electrostatic forces operating on the reaction center. This allows using a myriad of detection methods in order to determine the presence of fungi and other organisms.

The present inventors have further envisioned that such an adduct, which eventually alters the structural and/or electronic features of ergosterol, could be efficiently used an immunogenic moiety. Thus, it was envisioned that such an adduct could be utilized for constructing an ergosterol-based immunoassay for detecting fungi and other organisms, upon utilizing it to produce ergosterol-selective antibodies.

While reducing the present invention to practice, the present inventors successfully prepared and practiced Diels-Alder adducts of ergosterol, and have showed that such an adduct can be efficiently used for detecting the presence of fungi. Thus, it has been demonstrated that ergosterol can serve as an efficient biomarker for the presence of fungi, upon forming a detectable conjugate containing same.

Hence, according to one aspect of the present invention there is provided a method of determining a presence and/or a level of an ergosterol-containing organism in a substrate. The method, according to this aspect of the present invention, is effected by contacting at least a portion of the substrate with a compound that is capable of forming a conjugate with ergosterol and determining the presence and/or level of the conjugate. As discussed hereinabove, since ergosterol is uniquely present in fungi and other specific organisms, the presence and/or level of the conjugate is indicative of the presence and/or level of ergosterol and hence is indicative of the presence and/or level of such organisms in the substrate.

As used herein, the phrase "ergosterol-containing organism" encompasses any organism, preferably a microorganism, which has ergosterol as a predominant sterol. These particularly include fungi, as well as other parasites such as leishmaniasis and protists, such as trypanosomes.

As used herein, the phrase "determining a presence and/or a level" describes quantitative, semi-quantitative and/or qualitative detection of a substance (e.g., a fungus, a conjugate, a complex, etc.). This phrase is therefore also referred to herein, interchangeably, as "detecting".

The phrase "at least a portion" describes either a portion of the substrate or the whole substrate, whereby the portion of the substrate can be a physical portion (namely, an area within a surface of a substance, or a certain volume of a liquid substance), or a chemical portion (namely, a portion obtained upon extraction or isolation of certain components).

In one embodiment, the portion of a substrate is a sterol-containing portion of the substrate and the method is further effected by isolating such a portion. The isolation is preferably effected by subjecting the substrate to extraction, using organic, hydrophobic solvents.

In a preferred embodiment, isolating the sterol-containing portion is effected prior to the contacting with the compound that forms a conjugate with ergosterol. By this, the relative concentration of the ergosterol, if present, is increased and hence the reaction with the compound is facilitated. However, such an isolation can further be effected subsequent to contacting the substrate with the compound.

As used herein, the phrase "conjugate" describes a chimeric compound which comprises two moieties that are covalently linked therebetween. Each of these moieties is derived from a compound forming the conjugate and represents the part of the compound that is present within the conjugate upon the formation of the covalent bond. For example, a moiety of ergosterol upon forming a Diels-Alder adduct thereof is a structure that corresponds to the ergosterol structure but has a 5,6-double bond instead of the 5,7-diene moiety. Herein throughout the moieties forming the conjugate are referred to as the compounds before conjugation, whereas the nature of the moiety of each compound that is formed upon conjugation should be readily recognized by any person skilled in the art.

Each of the conjugates described herein includes an ergosterol moiety, formed upon covalently linking ergosterol to another compound. These conjugates are also referred to herein, interchangeably, as "ergosterol-containing conjugates".

The phrase "compound capable of selectively forming a conjugate with ergosterol" describes any compound that has a structure and functionality that allows the formation of a covalent bond with ergosterol. By "selectively" it is meant that the compound has a structure and functionality that are favorable towards forming a covalent bond with ergosterol, as compared with other structurally related compounds (e.g., other sterols, such as cholesterol). A compound capable of selectively forming a conjugate with ergosterol is also referred to herein throughout simply as "compound".

As discussed hereinabove, preferred compounds for selectively forming a conjugate with ergosterol are compounds capable of interacting with the diene moiety of the ergosterol. More preferably, the compound is capable of interacting with the diene moiety of ergosterol so as to form a Diels-Alder adduct and is hence a dienophile. While there are other 1,3-diene-containing sterols, the methodology described herein allows to efficiently detect only the adducts formed with ergosterol, as is further detailed hereinbelow.

As used herein, the term "dienophile" describes a compound which can interact with a 1,3-diene in a Diels-Alder cycloaddition reaction. Dienophiles are typically unsaturated compounds, having a double bond or a triple bond, which is further typically substituted by at least one electron withdrawing group substituent.

Preferred dienophiles according to the present invention can therefore be collectively represented by the following general formula:

wherein:

X is N or CR3;

Y is N or CR4;

R3 and R4 are each independently selected from the group consisting of hydrogen, alkyl, cycloalkyl or, alternatively, R3 and R4 together form a bond; and R1 and R2 are each independently selected from the group consisting of hydrogen, alkyl, cycloalkyl, halide, hydroxy, amine, thiol, aryl and an electron withdrawing group, or, alternatively, R1 and R2 together form a bridging moiety, provided that at least one of R1 and R2 is an electron withdrawing group or that said bridging moiety comprises at least one electron withdrawing group.

Thus, the compound is preferably an alkene, alkyne, diazene, or carbazene (having a —C=N— moiety), each being preferably substituted by at least one electro withdrawing group, as defined herein.

The substituents R1 and R2 can optionally form a bridging moiety that comprises at least one electron withdrawing groups. Such bridging moieties form a cyclic dienophile, which has the following formula:

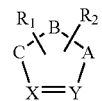

wherein X, Y, R1 and R2 are as defined above and A, B and C represent a carbon, sulfur, and/or nitrogen atom or an alkylene chain, each being optionally substituted by R1 and/or R2.

In general, cyclic dienophiles are more reactive than linear dienophiles and hence are presently preferred.

Representative examples of commonly used cyclic dienophiles that can be utilized in the context of the present embodiments include substituted or unsubstituted 2,3-dihydrophthalazine-1,4-diones and [1,2,4]-triazole-3,5-diones.

According to the presently most preferred embodiments, the dienophile is a substituted or unsubstituted, preferably substituted, [1,2,4]-triazole-3,5-dione, collectively referred to herein as TAD.

As used herein the phrase "electron withdrawing group" describes a substituent that draws electrons away from a reaction center. Representative examples include, but are not limited to, carboxylate, carbonyl, aldehyde, nitro, and nitrile.

As used herein, the term "alkyl" describes a saturated aliphatic hydrocarbon including straight chain and branched chain groups. Preferably, the alkyl group has 1 to 20 carbon atoms, more preferably 1-10 carbon atoms and more preferably 1-6 carbon atoms. The alkyl group may be substituted or unsubstituted.

A "cycloalkyl" group describes an all-carbon monocyclic or fused ring (i.e., rings which share an adjacent pair of carbon atoms) group wherein one or more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted.

An "alkenyl" group describes an alkyl or cycloalkyl group which consists of at least two carbon atoms and at least one carbon-carbon double bond.

An "alkynyl" group describes an alkyl group which consists of at least two carbon atoms and at least one carbon-carbon triple bond.

An "aryl" group describes an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted.

A "heteroaryl" group describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted.

A "heteroalicyclic" group describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Representative examples are piperidine, piperazine, tetrahydrofurane, tetrahydropyrane, morpholino and the like.

A "hydroxy" group describes an —OH group.

A "thiol" group (also referred to herein, interchangeably as "thiohydroxy") describes a —SH group.

An "azide" group describes a —N=N=N group.

An "alkoxy" group describes both an —O-alkyl and an —O-cycloalkyl group, as defined herein.

An "aryloxy" group describes both an —O-aryl and an —O-heteroaryl group, as defined herein.

A "thioalkoxy" group describes both an —S-alkyl group, and an —S-cycloalkyl group, as defined herein.

A "thioaryloxy" group describes both an —S-aryl and an —S-heteroaryl group, as defined herein.

A "halo" or "halide" group describes fluorine, chlorine, bromine or iodine.

An "amine" group describes an —NR'R" group where R' and R" are hydrogen, alkyl, cycloalkyl or aryl.

A "nitro" group describes an —NO$_2$ group.

A "nitrile" group describes a —C≡N group.

A "carboxylate" group describes a —C(=O)-L group, with L being hydroxy, alkoxy, thiohydroxy, thioalkoxy, aryloxy, thioaryloxy, halide, amine, or cycloalkyl, as these terms are defined herein.

A carbonyl group describes a —C(=O)—R group, with R being hydrogen (for aldehyde), alkyl, cycloalkyl, or aryl.

As discussed hereinabove, the compound capable of forming a conjugate with ergosterol is preferably selected so as to form a detectable conjugate.

Thus, in one embodiment, the compound comprises a detectable moiety.

As used herein, the term "detectable" describes a feature of a substance (a conjugate, compound or moiety) that allows identifying or tracing the substance by a detector, using known analytical techniques, as detailed hereinbelow.

Representative examples of detectable moieties include, without limitation, chromophores, fluorescent moieties, phosphorescent moieties, radioactive moieties, magnetic moieties (e.g., diamagnetic, paramagnetic and ferromagnetic materials), and heavy metal clusters, as is further detailed hereinbelow, as well as any other known detectable moieties.

As used herein, the term "chromophore" refers to a chemical moiety that when attached to a substance renders the latter colored and thus visible when various spectrophotometric measurements are applied.

A heavy metal cluster can be, for example, a cluster of gold atoms used, for example, for labeling in electron microscopy or X-ray imaging techniques.

As used herein, the phrase "fluorescent moiety" refers to a moiety that emits light at a specific wavelength during exposure to radiation from an external source.

As used herein, the phrase "phosphorescent moiety" refers to a moiety that emits light without appreciable heat or external excitation, as occurs for example during the slow oxidation of phosphorous.

As used herein, the phrase "radioactive moiety" encompasses any chemical moiety that includes one or more radioactive isotopes. A radioactive isotope is an element which emits radiation above the background radiation level. Examples include α-radiation emitters, β-radiation emitters or γ-radiation emitters.

The phrase "magnetic moiety" describes a moiety that is influenced by the presence of a magnetic field so as to exhibit a measurable property (e.g., magnetic resonance).

The detectable moiety is selected such that determining the presence and/or level of the conjugate is effected by determining a presence and/or a level of a signal produced by the detectable moiety.

Thus, the method, according to this aspect of the present can be effected by determining the presence and/or level of the conjugate directly upon contacting the substrate or a portion thereof with the conjugate. In a preferred embodiment, determining the presence of the conjugate is effected by subjecting the mixture formed upon contacting the compound and the substrate to a chromatographic assay, e.g., HPLC, and quantitatively, semi-quantitatively or qualitatively measuring the presence of the ergosterol-containing conjugate, preferably by spectrophotometric means, as detailed below.

According to other preferred embodiments of this aspect of the present invention, the method is effected by utilizing a recognizing substance that is capable of selectively binding the conjugate, so as to form a complex therewith and measuring the presence and/or level of the complex. Evidently, the recognizing substance is selected such that the presence and/or level of the complex is indicative of the presence and/or level of the conjugate and hence of the presence and/or level of a fungus or any other ergosterol-containing organism.

According to these embodiments, upon contacting the substrate with the compound capable of forming the conjugate, the resulting mixture is contacted with the recognizing substance. Alternatively, the substrate is contacted with the recognizing substance and the compound concomitantly. Optionally, the compound forms a part of the recognizing substance, as is exemplified hereinbelow.

Further according to these embodiments, the recognizing substance comprises a detectable moiety, as defined herein. Alternatively, the conjugate comprises a detectable moiety.

As used herein, the phrase "recognizing substance" describes a substance or a moiety that is designed so as to selectively bind the conjugate described herein and hence "recognizes" the presence of the conjugate within a medium that can optionally contain other compounds. The recognition of such a substance results from high-affinity attractive interactions with the conjugate, which are preferably higher as compared with its interactions with other substances.

In one exemplary embodiment, the recognizing substance is a quartz crystal having the compound capable of forming a conjugate with ergosterol attached thereto (e.g., to a gold surface of a quartz crystal microbalance plate). In the presence of ergosterol, the conjugate is formed onto the surface and as a result a change in the crystal frequency is effected. This frequency change is indicative of the presence and/or level of ergosterol and hence of the presence and/or level of a fungus or other ergosterol-containing organism (see, FIGS. 6a and 6b). For further details of this methodology please see Example 6 in the Examples section that follows.

In another exemplary embodiment, the recognizing substance is an antibody capable of selectively binding ergosterol and/or an ergosterol-containing conjugate.

As discussed hereinabove, a conjugate, preferably a Diels-Alder adduct, of ergosterol can be advantageously utilized for inducing an immunogenic response, to thereby produce the above-described selective antibodies and overcome the non-immunogenity of ergosterol. The antibodies thus produced can therefore serve as a recognizing substance according to these embodiments of the present invention.

An exemplary protocol for detecting fungi while utilizing such antibodies as a recognizing substance is as follows:

A sterol-containing portion is isolated from the substrate and is contacted with the compound described herein. The obtained mixture is then contacted with the selective antibody and the presence or absence of an antibody-ergosterol-containing conjugate is determined.

Various assay principles of the above described protocol are described in detail in Example 3 in the Examples section that follows. See also FIGS. 4a-4c.

Thus, determining the presence or absence of the complex, as well as quantification of the complex can be effected by various protocols, using various analytical techniques. This determination can be effected, for example, by utilized a detectable conjugate, or, alternatively, a detectable antibody. Any of the common techniques utilized in immunoassays, as detailed hereinbelow, can be applied herein.

In another exemplary embodiment, the recognizing substance is an antibody mimicry designed to selectively bind ergosterol and/or the ergosterol-containing conjugate. Antibody mimicries are widely taught in the art and typically include synthetic host-molecules designed so as to bind a specific guest-molecule. The host molecule is typically an organic compound whose binding sites are arranged in a specific spatial arrangement so as to fit the binding sites of the guest component (herein, ergosterol).

Exemplary recognizing substances in this category include, without limitation, molecularly imprinted polymers (MIPs), cavitands, clathrates, cryptands, cyclodextrins, calixarenes, cucurbiturils, porphyrins, crown ethers and triazines.

According to a preferred embodiment, the recognizing substance is a molecularly imprinted polymer.

The subject of molecularly imprinted polymers has been extensively reviewed (see, for example, Mosbach, K., et al., *TIBS*, 1994, 19, 9-14; Shea, K. J, 1994, *TRIP*, 5, 166 173; Kempe, M., Mosbach, K., 1995, *J. Chromatography A*, 694, 3-13; G. Wulff, *Angew. Chem., Int. Ed. Engl.* 1995, 34, 1812-1832; A. G. Mayyes and K. Mosbach, *Trends Anal. Chem.* 1997, 16, 321-332; 33, 23-26; K. Haupt and K. Mosbach, *Trends Biotechnol.* 1998, 16, 468-475; R. A. Bartsch and M. Maeda, Eds. 1998, *'Molecular and Ionic Recognition with Imprinted Polymers'* ACS Symp. Ser. 703; American Chemical Society, Washington, D.C.; Sellergren, B. 2001, *'Molecularly imprinted polymers: man-made mimics of antibodies and their applications in analytical* chemistry, Elsevier, Amsterdam; N.Y. and a number of patents on this topic have been issued such as, for example, U.S. Pat. Nos. 4,127,730, 5,110,833, 5,630,978, 5,587,273, 5,872,198, 6,322,834, 6,379,599, 6,391,359, 6,638,498, 6,759,488, 6,783,686, 6,849,701, 6,852,818 and 7,041,762).

Briefly, the technique involves the polymerization of functional monomers in the presence of a template molecule. The functional monomers bind to active sites on the template molecule, either covalently or non-covalently, and are then polymerized, typically in the presence of excess of cross-linking agents. While the polymerization is effected in the presence of the template molecules, subsequent removal of the latter leaves behind cavities that, in an idealized view, have a shape and an arrangement of functional groups which is complementary to that of the template molecule, and thus the resulting MIP exhibits the ability to rebind the template molecule tightly and selectively.

When utilized in the context of the present embodiments, molecularly imprinted polymers can be designed and practiced according to a variety of protocols, some are described and exemplified in Example 5 of the Examples section that follows.

Thus, for example, a MIP can be prepared by polymerizing pre-selected monomers that interact with functional groups of an ergosterol-containing conjugate, in the presence of the conjugate. Such a MIP can selectively bind the ergosterol-containing conjugate and hence can be utilized for determining the presence and/or level of the conjugate. Using such a methodology, detecting the conjugate can be effected with a MIP that comprises a detectable moiety attached thereto, as described in detail in the Examples section and is further illustrated in FIG. 5. The detectable moiety can, for example, form a part of a detectable ergosterol-containing conjugate which is loaded into the MIP and is released upon forming a complex between the MIP and the conjugate obtained upon contacting the compound with the substrate. In this methodology, the detectable conjugate should be selected so as to have affinity interactions with the MIP that are weaker than those of the conjugate to be determined.

Alternatively, the MIP can be designed so as to have a moiety that is capable of forming a conjugate (e.g., an adduct) with ergosterol attached thereto. Such a moiety is used to selectively attach ergosterol. This moiety can therefore be derived from any of the compounds described herein. However, preferably, the moiety is attached to the MIP such that its capability to interact with ergosterol is maintained.

Determining the presence or level of a conjugate formed between ergosterol and the selected compound can be effected by any of the known analytical techniques. These include, for example, a chromatographic assay, a spectroscopic assay, an electron microcopy, a spectrophotometric assay, a radioactivity assay, an electrochemical assay, a quartz crystal microbalance assay, an immunoassay and any combination thereof. The assay can be either a competitive or non-competitive assay.

The analytical technique selected for determining the presence or level of the conjugate depends on the detectable properties of the conjugate or, vice versa, the detectable properties of the conjugate are selected so as to suit a desired analytical technique.

Spectrophotometric assays include, without limitation, phosphorescence assays, fluorescence assays, chromogenic assays, and luminescence assays.

Phosphorescence assays monitor changes in the luminescence produced by a spectrophotometrically detectable moiety after absorbing radiant energy or other types of energy. Phosphorescence is distinguished from fluorescence in that it continues even after the radiation causing it has ceased.

Fluorescence assays monitor changes in the luminescence produced by a spectrophotometrically detectable moiety under stimulation or excitation by light or other forms of electromagnetic radiation or by other means. The light is given off only while the stimulation continues; in this the phenomenon differs from phosphorescence, in which light continues to be emitted after the excitation by other radiation has ceased.

Chromogenic assays monitor changes in color of the assay medium produced by a spectrophotometrically detectable moiety which has a characteristic wavelength.

Luminescence assays monitor changes in the luminescence produced by a chemiluminescent moiety. Luminescence is caused by the movement of electrons within a substance from more energetic states to less energetic states.

The phrase "spectrophotometrically detectable" as used in the context of the present invention describes a physical phenomena pertaining to the behavior of measurable electromagnetic radiation that has a wavelength in the range from ultraviolet to infrared. The phrase "spectrophotometrically detectable moiety" therefore describes a moiety, which is characterized by one or more spectrophotometrically detectable properties, as defined hereinabove.

Chromatographic assays are based on the variable mobility of a substance through a certain media, which is turn depends on the interactions of the substance with the media and include, for example, gas chromatography (GC), high-performance liquid chromatography (HPLC), ion exchange chromatography, thin layer chromatography and column chromatography. When subjected to chromatographic assays, a substance or substances are typically identified by spectral means, e.g., by spectroscopic or spectrophotometric measurements.

Spectroscopic assays are based on spectral properties exerted by a substance when subjected to an external energy. The external energy can be, for example, a magnetic field, X-ray radiation, ionizing energy, an electron beam and the like, whereby spectroscopic assays include, for example, mass spectroscopy, NMR, electron microscopy (e.g., electron spinning resonance measurements), and the like.

Radioactivity assays measure the radioactive radiation emitted from a substance. Examples include positron emission tomography (PET) and single photon emission computed tomography (SPECT).

Electrochemical assays measure an electric current that is formed upon a redox reaction.

Immunoassays is a term used to collectively describe methods for the determination of chemical substances that utilize the highly specific binding between an antigen or hapten and homologous antibodies, including radioimmunoassay, enzyme immunoassay, and fluoroimmunoassay. In immunoassays, either the antibody or the antigen or hapten is labeled by e.g., an enzyme, a fluorescent moiety or a radioactive moiety, and the labeled moieties are detected using the corresponding analytical measurements.

The following describes some of the most commonly used immunoassays.

Enzyme-linked immunosorbent assay (ELISA): this method involves fixation of a sample containing a substrate to a surface such as a well of a microtiter plate. A substrate-specific antibody coupled to an enzyme is applied and allowed to bind to the substrate. Presence of the antibody is then detected and quantified by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Radioimmunoassay (RIA): In one version, this method involves precipitation of the desired substance with a specific antibody and radiolabeled antibody-binding protein immobilized on a precipitable carrier such as agarose beads. The radio-signal detected in the precipitated pellet is proportional to the amount of the bound substance.

In an alternate version of RIA, a labeled substance and an unlabelled antibody-binding protein are employed. A sample containing an unknown amount of substance is added in varying amounts. The number of radio counts from the labeled substance-bound precipitated pellet is proportional to the amount of substance in the added sample.

Fluorescence-activated cell sorting (FACS): This method involves detection of a substance in situ in cells bound by substance-specific, fluorescently labeled antibodies. The substance-specific antibodies are linked to fluorophores. Detection is by means of a cell-sorting machine, which reads the wavelength of light emitted from each cell as it passes through a light beam. This method may employ two or more antibodies simultaneously.

Immunohistochemical analysis: This method involves detection of a substance in situ in fixed cells by substance-specific antibodies. The substance specific antibodies may be enzyme-linked or linked to fluorophores. Detection is by microscopy, and is either subjective or by automatic evaluation. With enzyme-linked antibodies, a colorimetric reaction may be required.

The methodology described herein, utilizing a compound that is capable of selectively forming a conjugate with ergosterol, can be used to determine the presence and/or level of a fungus and other ergosterol-containing organisms in a variety of substrates.

As discussed hereinabove, novel methods for detecting fungal infections, as well as infections caused by other organisms, are highly desirable. As is demonstrated in the Examples section that follows, the methodology described herein can been successfully practiced for detecting the presence of various fungi, allowing a cost-effective, fast and accurate diagnosis that circumvents the need to performed laborious culturing assays.

Hence, according to preferred embodiments of the present invention, the methodology described herein is utilized for detecting a fungal infection in a subject. Thus, the substrate is preferably a bodily substrate, including, organs, tissues and cells. This methodology can further be utilized for detecting infections caused by other ergosterol-containing organisms.

Any organs, tissues and cells can serve as substrates, according to these embodiments, whereby contacting the substrate with the compound described herein can be effected either in vivo or in vivo, depending on the selected substrate.

Thus, for example, detecting a fungal infection in or about a nail is preferably effected in vivo, by contacting the nail with the compound and determining the presence and/or level of a corresponding ergosterol-containing conjugate.

Similarly, fungal infections in other "topical" organs such as mucosal membranes, genital organs, skin, ears and the like can be effected in vivo.

Invasive fungal infections are preferably detected by contacting the compound and the tested substrate in vitro. Blood samples are preferred substrates in this regard.

In addition to being used in diagnostics, the methodology described herein can be utilized for detecting the presence and/or level of a fungus in other substrates. These include, but are not limited to, any surface, structure, product or material which can support, harbor or promote the growth of a fungus. Non-limiting examples include the inner walls of a storage container that is routinely treated with anti-microbial preferably anti-fungal agents, a soil and/or soil enrichment supplements, any agricultural product or crop such as wood, fiber, fruit, vegetable, flower, extract, horticultural crop and any other processed or unprocessed agricultural product or crop which are produced from organic origins such as living plants or animals, a cosmetic product, a food product, a building, warehouse, compartment, container or transport vehicle, a dye or a paint and any other materials and industrial compounds used for which require protection of their surfaces against fungi attacks, such as, for example, construction materials.

Since ergosterol is present substantially in all fungi, the methodology described herein can be utilized for determining the presence and/or level of a very broad spectrum of fungi. Obviously, this methodology can further be utilized to determine the presence and/or level of any other organism or microorganism that contains ergosterol.

Representative examples of fungi that can be detected using the methodology described herein include, without limitation, the following list of genus and particulars in each genus: genus *Obsidian*: *Obsidian corymbifera*; genus *Ajellomyces*: *Ajellomyces capsulatus*, *Ajellomyces dermatitidis*; genus *Arthroderma*: *Arthroderma benhamiae*, *Arthroderma fulvum*, *Arthroderma gypseum*, *Arthroderma incurvatum*, *Arthroderma otae*, *Arthroderma vanbreuseghemii*; genus *Aspergillus*: *Aspergillus flavus*, *Aspergillus fumigatus*, *Aspergillus niger*; genus *Blastomyces*: *Blastomyces dermatitidis*; genus *Candida*: *Candida albicans*, *Candida glabrata*, *Candida guilliermondii*, *Candida krusei*, *Candida parapsilosis*, *Candida tropicalis*, *Candida pelliculosa*; genus *Cladophialophora*: *Cladophialophora carrionii*; genus *Coccidioides*: *Coccidioides immitis*; genus *Cryptococcus*: *Cryptococcus neoformans*; genus *Cunninghamella*: *Cunninghamella* sp.; genus *Epidermophyton*: *Epidermophyton floccosum*; genus *Exophiala*: *Exophiala dermatitidis*; genus *Filobasidiella*: *Filobasidiella neoformans*; genus *Fonsecaea*: *Fonsecaea pedrosoi*; genus *Fusarium*: *Fusarium solani*; genus *Geotrichum*: *Geotrichum candidum*; genus *Histoplasma*: *Histoplasma capsulatum*; genus *Hortaea*: *Hortaea werneckii*; genus *Issatschenkia*: *Issatschenkia orientalis*; genus *Madurella*: *Madurella grisae*; genus *Malassezia*: *Malassezia furfur*, *Malassezia globosa*, *Malassezia obtusa*, *Malassezia pachydermatis*, *Malassezia restricta*, *Malassezia slooffiae*, *Malassezia sympodialis*; genus *Microsporum*: *Microsporum canis*, *Microsporum fulvum*, *Microsporum gypseum*; genus *Mucor*: *Mucor circinelloides*; genus *Nectria*: *Nectria haematococca*; genus *Paecilomyces*: *Paecilomyces variotii*; genus *Paracoccidioides*: *Paracoccidioides brasiliensis*; genus *Penicillium*: *Penicillium marneffei*; genus *Pichia*, *Pichia anomala*, *Pichia guilliermondii*; genus *Pneumocystis*: *Pneumocystis carinii*; genus *Pseudallescheria*: *Pseudallescheria boydii*; genus *Rhizopus*: *Rhizopus oryzae*; genus *Rhodotorula*: *Rhodotorula rubra*; genus *Scedosporium*: *Scedosporium apiospermum*; genus *Schizophyllum*: *Schizophyllum commune*; genus *Sporothrix*: *Sporothrix schenckii*; genus *Trichophyton*: *Trichophyton mentagrophytes*, *Trichophyton rubrum*, *Trichophyton verrucosum*, *Trichophyton violaceum*; and of the genus *Trichosporon*: *Trichosporon asahii*, *Trichosporon cutaneum*, *Trichosporon inkin*, *Trichosporon mucoides*.

Further according to the present embodiments, the methodology described herein can be further utilized for manufacturing a kit for determining a presence and/or a level of a fungus in a substrate.

Such a kit typically comprises a compound capable of forming a conjugate with ergosterol, as described herein, and can optionally comprise a detecting unit for determining a presence and/or a level of such a conjugate. The kit is optionally designed as a portable kit, so as to allow performing the methodology also "on-the spot".

The detecting unit is selected according to the compound present in the kit. Thus, for example, a detecting unit that can be a unit utilized in any of the analytical techniques described herein. Alternatively the detecting unit can be simply an eye contact. The detecting unit can form a part of the kit, or can be operated elsewhere (e.g., in a laboratory).

Preferably, the kit further comprises a solid support such as, for example, a microtiter plate.

Further preferably, the kit comprises a recognizing substance, as described herein. Such a recognizing substance allows to readily construct a kit that can be conveniently used as it allows a selective detection of the desired substance (e.g., a complex, a conjugate).

In an exemplary embodiment, the recognizing substance is attached to the solid support and the tested sample (analyte) is contacted with the support. The resulting product is thereby tested using the detecting unit.

In another exemplary embodiment, the compound for forming a conjugate with ergosterol is attached to the solid support. In this case, the tested sample is contacted with the compound and the resulting mixture is then contacted with the recognition substance.

In still another embodiment, the compound and/or the recognition substance are individually packaged within the kit. One of these can be attached to a solid support, if desired only during the detection operation.

Any of the recognizing substances described herein can be utilized within the kit, using any of the exemplary assay principles described herein. In cases where the recognizing substance is a quartz crystal microbalance plate, such a plate can serve as a solid support to which the compound is attached. The attachment can be performed prior to or during the detection procedure.

As discussed hereinabove, the methodology described herein, utilizing an ergosterol-containing conjugate, can be successfully practiced for producing ergosterol-selective antibodies. Such a methodology is particularly advantageous when the conjugate is a Diels-Alder adduct of ergosterol, as discussed herein.

Hence, according to another aspect of the present invention there is provided an antibody comprising an antigen recognition domain capable of specifically binding to ergosterol.

The antibody can specifically bind ergosterol or, alternatively, can be designed to specifically bind an ergosterol-containing conjugate, comprising a compound covalently attached to ergosterol. Preferably the conjugate is a Diels-Alder adduct of ergosterol and a dienophiles, as described herein. More preferably it is an ergosterol-TAD adduct.

As used herein, the term "antibody" refers to a substantially intact antibody molecule and encompasses also an antibody fragment.

As used herein, the phrase "antibody fragment" refers to a functional fragment of an antibody that is capable of binding to an antigen.

Suitable antibody fragments for practicing the present invention include, inter alia, a complementarity-determining region (CDR) of an immunoglobulin light chain (referred to herein as "light chain"), a CDR of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as an Fv, a single-chain Fv, an Fab, an Fab', and an F(ab')2.

Functional antibody fragments comprising whole or essentially whole variable regions of both light and heavy chains are defined as follows:

(i) Fv, defined as a genetically engineered fragment consisting of the variable region of the light chain and the variable region of the heavy chain expressed as two chains;

(ii) single-chain Fv ("scFv"), a genetically engineered single-chain molecule including the variable region of the light chain and the variable region of the heavy chain, linked by a suitable polypeptide linker.

(iii) Fab, a fragment of an antibody molecule containing a monovalent antigen-binding portion of an antibody molecule, obtained by treating whole antibody with the enzyme papain to yield the intact light chain and the Fd fragment of the heavy chain, which consists of the variable and CH1 domains thereof;

(iv) Fab', a fragment of an antibody molecule containing a monovalent antigen-binding portion of an antibody molecule, obtained by treating whole antibody with the enzyme pepsin, followed by reduction (two Fab' fragments are obtained per antibody molecule); and (v) F(ab')2, a fragment of an antibody molecule containing a monovalent antigen-binding portion of an antibody molecule, obtained by treating whole antibody with the enzyme pepsin (i.e., a dimer of Fab' fragments held together by two disulfide bonds).

Further according to the present invention there is provided a process of producing the antibodies described herein. The process is effected by inducing an immunogenic response (immunization) to a conjugate of ergosterol and a compound being covalently attached thereto, as described herein, to thereby produce the antibody, and collecting the antibody. Exemplary protocols of this process are described in detail in the Examples section that follows.

Methods of generating monoclonal and polyclonal antibodies are well known in the art. Antibodies may be generated via any one of several known methods, which may employ induction of in vivo production of antibody molecules, screening of immunoglobulin libraries (Orlandi, R. et al. (1989). Cloning immunoglobulin variable domains for expression by the polymerase chain reaction. Proc Natl Acad Sci USA 86, 3833-3837; and Winter, G. and Milstein, C. (1991). Man-made antibodies. Nature 349, 293-299), or generation of monoclonal antibody molecules by continuous cell lines in culture. These include, but are not limited to, the hybridoma technique, the human B-cell hybridoma technique, and the Epstein-Barr virus (EBV)-hybridoma technique (Kohler, G. and Milstein, C. (1975). Continuous cultures of fused cells secreting antibody of predefined specificity. Nature 256, 495-497; Kozbor, D. et al. (1985). Specific immunoglobulin production and enhanced tumorigenicity following ascites growth of human hybridomas. J Immunol Methods 81, 31-42; Cote R J. et al. (1983). Generation of human monoclonal antibodies reactive with cellular antigens. Proc Natl Acad Sci USA 80, 2026-2030; and Cole, S. P. et al. (1984). Human monoclonal antibodies. Mol Cell Biol 62, 109-120).

Suitable subjects in which inducing immunization can be effected preferably include mammalian subjects such as mice, rabbits, and others. Suitable protocols involve repeated injection of the immunogen in the presence of adjuvants according to a schedule designed to boost production of antibodies in the serum. The titers of the immune serum can readily be measured using immunoassay procedures which are well known in the art.

The antisera obtained can be used directly or monoclonal antibodies may be obtained, as described hereinabove.

Antibody fragments may be obtained using methods well known in the art (See, for example, Harlow, E. and Lane, D. (1988). Antibodies: A Laboratory Manual, Cold Spring Harbor Laboratory, New York.). For example, antibody fragments according to the present invention can be prepared by proteolytic hydrolysis of the antibody or by expression in $E.$ $coli$ or mammalian cells (e.g., Chinese hamster ovary (CHO) cell culture or other protein expression systems) of DNA encoding the fragment.

Alternatively, antibody fragments can be obtained by pepsin or papain digestion of whole antibodies by conventional methods. As described hereinabove, an (Fab')$_2$ antibody fragments can be produced by enzymatic cleavage of antibodies with pepsin to provide a 5S fragment. This fragment can be further cleaved using a thiol reducing agent, and optionally a blocking group for the sulfhydryl groups resulting from cleavage of disulfide linkages, to produce 3.5S Fab' monovalent fragments. Alternatively, enzymatic cleavage using pepsin produces two monovalent Fab' fragments and an Fc fragment directly. Ample guidance for practicing such methods is provided in the literature of the art (for example, refer to: U.S. Pat. Nos. 4,036,945 and 4,331,647; and Porter, R. R. (1959). The hydrolysis of rabbit γ-globulin and antibodies with crystalline papain. Biochem J 73, 119-126). Other methods of cleaving antibodies, such as separation of heavy chains to form monovalent light-heavy chain fragments, further cleavage of fragments, or other enzymatic, chemical, or genetic techniques may also be used, so long as the fragments retain the ability to bind to the antigen that is recognized by the intact antibody.

As described hereinabove, an Fv is composed of paired heavy chain variable and light chain variable domains. This association may be noncovalent (see, for example, Inbar, D. et al. (1972). Localization of antibody-combining sites within the variable portions of heavy and light chains. Proc Natl Acad Sci USA 69, 2659-2662). Alternatively, as described hereinabove, the variable domains may be linked to generate a single-chain Fv by an intermolecular disulfide bond, or alternately such chains may be cross-linked by chemicals such as glutaraldehyde.

Preferably, the Fv is a single-chain Fv. Single-chain Fvs are prepared by constructing a structural gene comprising DNA sequences encoding the heavy chain variable and light chain variable domains connected by an oligonucleotide encoding a peptide linker. The structural gene is inserted into an expression vector, which is subsequently introduced into a host cell such as $E.$ $coli$. The recombinant host cells synthesize a single polypeptide chain with a linker peptide bridging the two variable domains. Ample guidance for producing single-chain Fvs is provided in the literature of the art (see, e.g.: Whitlow, M. and Filpula, D. (1991). Single-chain Fv proteins and their fusion proteins. METHODS: A Companion to Methods in Enzymology 2(2), 97-105; Bird, R. E. et al. (1988). Single-chain antigen-binding proteins. Science 242, 423-426; Pack, P. et al. (1993). Improved bivalent miniantibodies, with identical avidity as whole antibodies, produced by high cell density fermentation of $Escherichia$ $coli$. Biotechnology (N.Y.) 11(11), 1271-1277; and U.S. Pat. No. 4,946,778).

Isolated complementarity-determining region peptides can be obtained by constructing genes encoding the CDR of an antibody of interest. Such genes may be prepared, for example, by RT-PCR of the mRNA of an antibody-producing cell. Ample guidance for practicing such methods is provided in the literature of the art (e.g., Larrick, J. W. and Fry, K. E. (1991). PCR Amplification of Antibody Genes. METHODS: A Companion to Methods in Enzymology 2(2), 106-110).

It will be appreciated that for human diagnostics, humanized antibodies are preferably used. Humanized forms of non-human (e.g., murine) antibodies are genetically engineered chimeric antibodies or antibody fragments having (preferably minimal) portions derived from non-human antibodies. Humanized antibodies include antibodies in which the CDRs of a human antibody (recipient antibody) are replaced by residues from a CDR of a non-human species (donor antibody), such as mouse, rat, or rabbit, having the desired functionality. In some instances, the Fv framework residues of the human antibody are replaced by corresponding non-human residues. Humanized antibodies may also comprise residues found neither in the recipient antibody nor in the imported CDR or framework sequences. In general, the humanized antibody will comprise substantially all of at least one, and typically two, variable domains, in which all or substantially all of the CDRs correspond to those of a non-human antibody and all or substantially all of the framework regions correspond to those of a relevant human consensus sequence. Humanized antibodies optimally also include at least a portion of an antibody constant region, such as an Fc region, typically derived from a human antibody (see, for example: Jones, P. T. et al. (1986). Replacing the complementarity-determining regions in a human antibody with those from a mouse. Nature 321, 522-525; Riechmann, L. et al. (1988). Reshaping human antibodies for therapy. Nature 332, 323-327; Presta, L. G. (1992b). Curr Opin Struct Biol 2, 593-596; and Presta, L. G. (1992a). Antibody engineering. Curr Opin Biotechnol 3(4), 394-398).

Methods for humanizing non-human antibodies are well known in the art. Generally, a humanized antibody has one or more amino acid residues introduced into it from a source which is non-human. These non-human amino acid residues are often referred to as imported residues, which are typically taken from an imported variable domain. Humanization can be performed essentially as described (see, for example: Jones et al. (1986); Riechmann et al. (1988); Verhoeyen, M. et al. (1988). Reshaping human antibodies: grafting an antilysozyme activity. Science 239, 1534-1536; and U.S. Pat. No. 4,816,567), by substituting human CDRs with corresponding rodent CDRs. Accordingly, humanized antibodies are chimeric antibodies, wherein substantially less than an intact human variable domain has been substituted by the corresponding sequence from a non-human species. In practice, humanized antibodies may be typically human antibodies in which some CDR residues and possibly some framework residues are substituted by residues from analogous sites in rodent antibodies.

Human antibodies can also be produced using various additional techniques known in the art, including phage-display libraries (Hoogenboom, H. R. and Winter, G. (1991). By-passing immunization. Human antibodies from synthetic repertoires of germline VH gene segments rearranged in vitro. J Mol Biol 227, 381-388; Marks, J. D. et al. (1991). By-passing immunization. Human antibodies from V-gene libraries displayed on phage. J Mol Biol 222, 581-597; Cole et al. (1985), Monoclonal Antibodies and Cancer Therapy, Alan R. Liss, Inc., pp. 77-96; and Boerner, P. et al. (1991). Production of antigen-specific human monoclonal antibodies from in vitro-primed human splenocytes. J Immunol 147, 86-95). Humanized antibodies can also be created by introducing sequences encoding human immunoglobulin loci into transgenic animals, e.g., into mice in which the endogenous immunoglobulin genes have been partially or completely inactivated. Upon antigenic challenge, human antibody production is observed in such animals which closely resembles that seen in humans in all respects, including gene rearrangement, chain assembly, and antibody repertoire. Ample guidance for practicing such an approach is provided in the literature of the art (for example, refer to: U.S. Pat. Nos. 5,545,807; 5,545,806; 5,569,825; 5,625,126; 5,633,425; and 5,661,016; Marks, J. D. et al. (1992). By-passing immunization: building high affinity human antibodies by chain shuffling. Biotechnology (N.Y.) 10(7), 779-783; Lonberg et al., 1994. Nature 368:856-859; Morrison, S. L. (1994). News and View: Success in Specification. Nature 368, 812-813; Fishwild, D. M. et al. (1996). High-avidity human IgG kappa monoclonal antibodies from a novel strain of minilocus transgenic mice. Nat Biotechnol 14, 845-851; Neuberger, M. (1996). Generating high-avidity human Mabs in mice. Nat Biotechnol 14, 826; and Lonberg, N. and Huszar, D. (1995). Human antibodies from transgenic mice. Int Rev Immunol 13, 65-93).

After antibodies have been obtained, they may be tested for activity, for example via enzyme-linked immunosorbent assay (ELISA).

Screening the obtained antibodies results in determining the best antibody to be used in the context of the present invention. As described herein, the antibody can be capable of selectively binding to ergosterol per se, or to the ergosterol-containing conjugate.

The above methodology can be used to produce antibodies to substances other than ergosterol, which are capable of forming an adduct, preferably a Diels-Alder adduct. As discussed hereinabove, adducts are conjugates that alter structural (and optionally electronic) features of a substance, as opposed to conjugates in which a substance is simply bearing an additional moiety) and hence can better improve the immunogenicity of the substance.

Thus, according to another aspect of the present invention there is provided a process of preparing an antibody which comprises an antigen recognition domain capable of specifically binding to a substance, which is effected by inducing an immunogenic response (immunization) to an adduct of the substance, preferably a Diels-Alder adduct of the substance, and isolating the antibodies formed thereby.

The substance can be any substance that is capable of forming an adduct with another compound.

As used herein the term "adduct" describes a conjugate of a substance and another compound, in which upon conjugation, the structural and/or electronic features of the original substance are changed. Such a change include a degree of saturation/unsaturation, the formation of a bridging moiety within the adduct, the formation of an additional or different ring structure, and the like.

Preferably the substance comprises a 1,3-diene moiety that is capable of forming a Diels-Alder adduct.

The immunization protocol, as well as other procedures for producing such antibodies, are delineated hereinabove.

Further according to the present invention there are provided synthetic antibody mimicries that are capable of selectively binding ergosterol, either per se or within an ergosterol-containing conjugate.

Such compounds typically comprise a substance having a structural affinity to ergosterol or to the ergosterol-containing conjugate and at least one functional group capable of forming an interaction with ergosterol or with the conjugate, respectively.

A "substance having a structural affinity" to ergosterol or a conjugate thereof means that the substance can bind the ergosterol or a conjugate thereof with substantially higher affinity as compared to other substances, due to the spatial arrangement of the functional and other groups therewithin.

The functional groups in such compounds can form with the ergosterol or the conjugate thereof covalent interactions or non-covalent interactions such as hydrogen bonds or hydrophobic interactions.

In one example, compounds capable of selectively binding ergosterol per se have a dienophile, as described herein, as a functional group, such that the dienophile forms a selective Diels-Alder adduct with ergosterol.

Compounds that have functional groups that are capable of selectively binding the ergosterol-containing conjugate can interact with the conjugate also via ionic interactions, depending on the nature of the functional groups of a desired conjugate.

These compounds can be any of the known antibody mimicries described herein. Preferably these compounds are MIPs capable of selectively binding ergosterol or a conjugate, preferably a Diels-Alder adduct, thereof.

Further according to the present invention there are provided processes of preparing the compounds described herein. These processes can be effected using any of the well-known methodologies described in the art for producing selective host-molecules. These processes can further be effected while screening libraries for the best functional groups, best substances that have a structural affinity to the desired molecule, etc.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Materials and Experimental Methods

Materials:
All chemicals were purchased from Sigma-Aldrich and were used without further purification unless otherwise indicated.

Serum samples and human whole blood samples on heparin (w.b.h.) were obtained from the blood center in Tel Hashomer hospital, Ramat Gan, Israel.

*Candida Allbicans* (C.a) ATCC deposit No. 90028 was cultured on a Sabouraud agar. Colonies were diluted with PBS to a final concentration of $10^5$ CFU.

Experimental Methods:
HPLC was performed using a JASCO instrument equipped with 875-UV Intelligent UV-VIS Detector, Hitachi F-1000 Fluorescence Detector, AS-2055 plus Intelligent Autosampler, PU-2089 plus Quaternary gradient Pump and HP Comaq Computer. Analysis was performed on a Phenosphere-NEXT 5µ, 250×4.6 mm C18 column. The UV detector was operated at 340 nm, and the fluorescence detection was operated with excitation at 342 nm and emission at 397 nm). Methanol was used as the mobile phase with flow rate of 1 ml/minute.

$^1$H NMR spectra were recorded on a Bruker DPX-250 MHz. Unless otherwise mentioned, the spectra were recorded in CDCl$_3$ with TMS as internal standard.

Column chromatography was carried out on Silica gel 60, 200-400 mesh (Merck).

TLC was performed on Merck silica 60 F$_{254}$ plated aluminum.

Sonication was performed using Elma sonicator D78224.

Mass spectra analyses were performed using Micromass, Platform LCZ 4000. Micromass, Manchester. UK. Ionization Mode: ESI—Electro Spray Ionization.

Example 1

Preparation of an Ergosterol-Triazolinedione Conjugate

Synthesis of 4-(3-Pyren-4-yl-propyl)-[1,2,4]triazole-3,5-dione-ergosterol Conjugate (Compound 4)

The preparation of an exemplary conjugate according to the present embodiment, a conjugate of ergosterol and 4-(3-pyren-4-yl-propyl)-[1,2,4]triazole-3,5-dione (pyrenyl propyl TAD), is schematically illustrated in Scheme 1 below. A fluorescent derivative of TAD was selected so as to allow detection of the formed conjugate during HPLC measurements and other analyses.

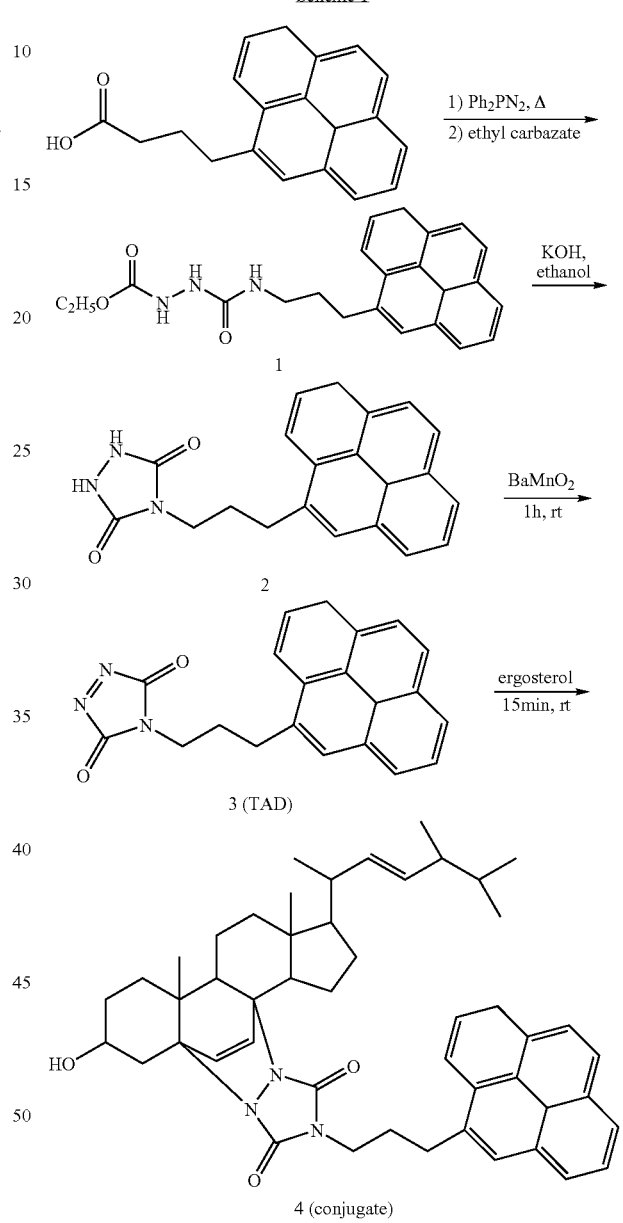

Scheme 1

Preparation of a Semicarbazide (Compound 1)

A solution of 3-pyren-1-yl butyric acid (800 mg, 2.7 mmol) in dry THF (25 ml) was stirred at 0° C. under argon atmosphere, and diphenylphosphoryl azide (500 µl, 2.45 mmol) was added thereto. Fifteen (15) minutes thereafter, triethylamine (650 µl, 2.45 mmol) was added and after 5 minutes the solution was removed from the ice-bath and was stirred at room temperature for 50 minutes. The solution was then heated at reflux, under nitrogen atmosphere, for 100 minutes and a solution of ethyl carbazate (285 mg, 2.7 mmol) in dry THF (5 ml) was then added to the boiling solution. After additional 20 minutes the solution was cooled to room temperature and concentrated under reduced pressure. Ethylacetate (100 ml) was thereafter added to the concentrate, and the obtained solution was washed with aqueous $NaHCO_3$, water, 1M HCl and water, dried over $Na_2SO_4$ and evaporated, yielding the crude semicarbazide (Compound 1). The crude semicarbazide was recrystallized from ethyl acetate, to yield an off-white powder (610 mg, 88% yield), having a purity higher than 99%, as determined by HPLC, as described hereinabove (Retention time: 8.2 minutes).

Preparation of a Urazol Derivative (Compound 2)

The semicarbazide Compound 1 (600 mg, 1.5 mmol) was dispersed in 20 ml 4N KOH and the mixture was heated to 85° C., to thereby obtain a clear solution. The solution was thereafter heated at 85° C. for additional hour and was then cooled to 0° C. and acidified to pH=2 with concentrated HCl. The resulting sticky precipitate was filtered through a N5 sinter glass filter and was dried at 70° C. overnight. The crude product was crystallized from a 1:1 methanol:water mixture, to give the urazol (Compound 2) as an off-white precipitate (300 mg, 66% yield), having a purity higher than 99%, as determined by HPLC, as described hereinabove (Retention time: 6.7 minutes).

TLC ($Si_{60}$ plate, ethyl acetate as eluent): Rf=0.2
$^1$H-NMR (DMSO-d6): δ=10.09 (brs, 2H), 7.99-8.34 (m, 9H), 3.58 (t, 2H), 3.35 (m, 2H), 2.07 (t, 2H) ppm.

Preparation of 4-(3-Pyren-4-yl-propyl)-[1,2,4]triazole-3,5-dione (Compound 3) and the Ergosterol-Triazolinedione Conjugate (Compound 4)

Urazol (Compound 2, 30 mg, 0.08 mmol) was mixed with 150 mg (0.59 mmol) of barium manganate. Ethyl acetate (10 ml) was thereafter added and the mixture was stirred for 50 minutes. The mixture was then filtered through Celite®, to afford a red solution of 4-(3-Pyren-4-yl-propyl)-[1,2,4]triazole-3,5-dione (pyrenyl propyl TAD, Compound 3). Compound 3 was added dropwise to a stirred solution of ergosterol (32 mg, 0.08 mmol) in ethyl acetate (20 ml), at room temperature. The red color disappeared. After 30 minutes of stirring at room temperature the mixture was evaporated to dryness, to give 62 mg of the crude product. The product was purified by silica gel column chromatography, using a mixture of ethyl acetate:petrol ether as eluent, and then crystallized from acetonitrile, to give Compound 4 as a white precipitate (8 mg, 15% yield) having a 99% purity as determined by HPLC, as described hereinabove (Retention time=15.1).

TLC ($Si_{60}$ plate, ethyl acetate as eluent): Rf=0.3
MS: m/z=779 (M+K)
HPLC Measurements:
In order to evaluate the capability of pyrenyl propyl TAD to serve as a quantitative and qualitative probe for detecting and determining the level of ergosterol, and to use the conjugate formed therebetween in the following assays, calibration measurements were performed as follows:

Stock solutions of the conjugate Compound 4 (140 nmol/ml) in MeOH, Ergosterol (100 nmol/ml) in EtOAc, and TAD (1000 nmol/ml) in EtOAc, were prepared and used for HPLC measurements and calibration curves.

Three series of calibration were monitored on HPLC:
(i) reaction of ergosterol with 5 molequivalents of TAD;
(ii) reaction of ergosterol with 10 molequivalents of TAD; and
(iii) reaction of ergosterol with 50 molequivalents of TAD.

Exemplary calibration curves, obtained for the reaction between increasing concentrations of ergosterol and 5 molequivalents and 10 molequivalents of the TAD are presented in FIGS. 1a and 1b, respectively, and clearly demonstrate the good linearity obtained in the HPLC measurements.

Using the procedure described hereinabove, other derivatives of TAD can be prepared, by using corresponding starting materials. These derivatives can be further reacted with ergosterol, as described herein, to form various ergosterol-TAD conjugates. Similarly, ergosterol is reacted with other dienophiles, as detailed herein, to thereby produce the corresponding ergosterol-dienophile conjugates via a Diels-Alder reaction.

Example 2

Extraction of Ergosterol from Serum by Conjugate Formation with TAD

Extraction Protocol:
The conditions for extracting the ergosterol from the serum were studied by spiking the serum with ergosterol, followed by extraction, according to the following general protocol:

Samples of serum (0.1 ml) were treated with different amounts of ergosterol (0.1 nmol, 1 nmol, 4 nmol, 10 nmol containing samples of a 100 nmol/ml solution in THF) and the obtained solutions were vortexed for several minutes. EtOH (0.1 ml) was then added to each tube and the solutions were extracted with hexane (2×0.5 ml) by shaking and sonicating for 3 minutes. The organic (hexane) layer was separated and evaporated by an air stream. Pyrenyl propyl TAD (Compound 3, excess of 10 equivalents in acetonitrile) was then added to the organic phase and the solution was vortexed. Acetonitrile was added to make-up a volume of 1 ml, the samples were filtered and subjected to HPLC analysis, as detailed hereinabove. The retention time of the conjugate was 15.1 minutes.

Experimental Results:
Good linearity was obtained for all of the four tested ergosterol concentrations, as exemplified in FIG. 2. Recovery of ergosterol from serum was from 65% to 73%. Detection limit was found to be about 0.1 nmol/ml of a 10 □l sample.

These results clearly demonstrate the probing capabilities of the fluorescent TAD derivative for ergosterol and the ability to use such a derivative for forming a conjugate with extracted ergosterol, which is indicative for the presence and level of ergosterol.

Example 3

Determination of Ergosterol in Clinical Samples Using Conjugate Formation with TAD Prior to determining ergosterol levels in clinical samples, extensive studies were conducted with samples containing an eatable fungi (e.f.) *Pseudorotus osteatus* or *Candida A.* and with blood samples spiked with *Candida A.*, using the following general protocol:

Samples are treated (saponified) with an alcoholic KOH solution, under reflux. The mixture is then cooled, water is added, followed by addition of hexane, and optionally further followed by sonication. The hexane is evaporated by an air stream and additional (1-2) portion(s) of hexane is/are added. Following evaporation of hexane, the dry residue is treated with a solution of a fluorescent TAD (e.g., Compound 3 hereinabove) in a polar solvent (e.g., acetonitrile) and the obtained mixture is then further diluted with acetonitrile to a final volume. Samples of the resulting solution are then subjected to a HPLC analysis, using fluorescence detection.

In an exemplary procedure, 10 ml of a 4% KOH/ethanol solution was added to 1 gram of wet mass (*Pseudorotus osteatus*), and the mixture was refluxed for 2 hours in a small Erlenmeyer flask equipped with a reflux condenser. The mixture was then cooled, and 5 ml of water were added followed by 20 ml of hexane. The mixture was sonicated for 3 minutes, the hexane phase was separated by a dropping funnel and the solvent was evaporated by an air stream. Additional hexane (20 ml) was thereafter added and the solution was extracted. The dry residue was treated with TAD solution in acetonitrile and diluted with acetonitrile to a final volume of 200 μl. Samples of 20 μl of the obtained mixture were subjected to HPLC analysis as described hereinabove. The obtained data indicated that the ergosterol-TAD conjugate was formed in most of tested samples (data not shown).

A flow chart illustrating another exemplary process for detecting ergosterol in fungus-containing samples is presented in FIG. 3a. In this process, ergosterol is extracted from blood samples spiked with *Candida Allbicans*, according to the protocol presented in FIG. 3b and is thereafter reacted with a labeled TAD derivative, to thereby form an adduct. The adduct is then analyzed (quantitatively and qualitatively) by HPLC.

Upon demonstrating the plausibility of the methodology described herein, clinical samples are tested, according to the following general protocol, and the obtained results are compared with culturing assays, performed as described in the Experimental Section.

A clinical sample (0.5-0.7 ml) is heated to reflux in 5 ml of 1% methanolic KOH for 1.5 hours. After cooling, 2 ml of water is added, and sterol components are extracted with n-hexane (twice with 6 ml). The combined hexane fractions are evaporated using a nitrogen stream and the residues are treated by freshly prepared TAD (Compound 3, 20 nmol) dissolved in acetonitrile (or otherwise in 2-propanol or ethanol). After 10 seconds of vortexing, the samples are dried in a nitrogen stream and dissolved in methanol for HPLC analysis using a fluorescence detector, as detailed hereinabove. Showing a consistency with the results obtained in the culturing assay demonstrates that applicability of the methodologies presented herein in detection of fungi.

Example 4

Detection of an Ergosterol-TAD Adduct by Immunoassay

General Protocols:

A general immunoassay for detecting ergosterol according to the present embodiments is based on interacting, on the surface of a microtiter plate, an ergosterol-dienophile adduct and an anti-ergosterol antibody, being specific to ergosterol or to the ergosterol-dienophile adduct, whereby the antibody and/or the adduct are labeled and hence produce a readable signal that is proportional to the level of ergosterol in the tested sample.

The above-described immunoassay can be performed via various assay principals, wherein in each assay principal either an antibody specific to ergosterol or to the ergosterol-dienophile adduct, ergosterol or a dienophile is bound to the microtiter plates, and either the dienophile or the antibody are labeled by a detectable moiety or are detectable upon an additional reaction or reactions cascade, as is detailed herein.

FIGS. 4a-c illustrate exemplary assay principles for detecting ergosterol in a sample by ergosterol-dienophile adduct-selective antibodies.

Thus, in one example, schematically illustrated in FIG. 4a, an ergosterol is extracted from a clinical sample and reacted with a labeled TAD (triazolinedione), as described hereinabove. The resulting labeled ergosterol-TAD adduct is then selectively captured by a specific antibody immobilized on a microtiter plate, which recognizes the modified molecule. The signal detected by a microtiter plate reader corresponds to the presence and quantity of the ergosterol bound to the antibody. The obtained (fluorescent) signal affords a qualitative or semi-quantitative estimation of ergosterol in the clinical sample.

In another example, schematically illustrated in FIG. 4b, an ergosterol is extracted from a clinical sample, as described hereinabove. A microtiter plate, chemically modified so as to have a dienophile precursor (e.g., a urazole TAD precursor; see, Compound 2 in Scheme 1 hereinabove) is activated so as to produce an active dienophile (e.g., a TAD derivative) for forming an adduct with the extracted ergosterol onto the plate. The modified plate is then contacted with a labeled/detectable antibody specific to ergosterol or the ergosterol adduct. The obtained signal affords a qualitative or semi-quantitative estimation of ergosterol in the clinical sample. Detecting the antibody is performed using fluorescent, radioactive, or enzymatic labels including bio- or chemiluminescent labels. The enzyme labels which may be used include, but are not limited to, color producing enzymes such as horse radish peroxidase ("HRP") and alkaline phosphatase ("AP"), and light producing enzymes such as luciferase. The antibodies can be used in a number of different diagnostic tests. Such assays include, but are not limited to, ELISA, Western blot, radioimmunoassay ("RIA"), bioluminescent assay, and chemiluminescent assay. Such immunoassays are well-known in the art and are further described in more detail herein.

In another example, schematically illustrated in FIG. 4c, an ergosterol is extracted from a clinical sample, as described hereinabove. The extracted ergosterol is thereafter competitively reacted with a microtiter plate, modified so as to have an ergosterol- or ergosterol-TAD adduct-specific antibody attached thereto, complexed with a labeled ergosterol-dienophile adduct. The obtained (fluorescent) signal affords a qualitative or semi-quantitative estimation of ergosterol in the clinical sample.

Immobilization of the antibody or the dienophile precursor to a microtiter plate is performed using a suitable and compatible procedure selected amongst the myriad of reactions known in the art.

Preparation of Antibodies for Ergosterol and/or Ergosterol-Dienophile Adduct

In each of the above-described protocols, antibodies specific to the ergosterol-dienophile adduct (e.g., ergosterol-TAD adduct) or simply to ergosterol are utilized. The following describes general protocols for producing such antibodies.

The general protocols involve developing suitable polyclonal and monoclonal antibodies and labeling the formed antibodies.

Production of Rabbit Antibodies for Ergosterol or Ergosterol-Dienophile Adduct:

An ergosterol-dienophile adduct, as described herein, is repeatedly injected to rabbits (n=2), optionally in the presence of adjuvants, according to a schedule designed to boost production of antibodies in the serum. Preferably, two boosts are performed in intervals of one month, so as to obtain 50-80 ml sera. The above procedure is performed with three different types of antigen complexes (e.g., adducts of ergosterol and different types of dienophiles).

The titers of the immune serum are then measured using immunoassay procedures well known in the art, to test the antibodies activity; the serum is thereafter purified on an affinity column, to thereby isolate the antibodies and the produced antibodies are screened, so as to select the antibodies exhibiting the best performance in terms of specificity, sensitivity and/or cross-reactivity with other sterols.

Production of Monoclonal Antibodies:

A combination of three different ergosterol-dienophile adducts, as described herein, is repeatedly injected to mice (n=5), optionally in the presence of adjuvants, according to a schedule designed to boost production of antibodies in the serum. Preferably, three boosts are performed in intervals of one month.

The titers of the immune serum are then measured using immunoassay procedures well known in the art, to test the antibodies activity; the serum is then purified on an affinity column and the produced antibodies are screened, so as to select the antibodies exhibiting he best performance in terms of specificity, sensitivity and/or cross-reactivity with other sterols.

The selected antibodies obtained in each of the protocols described above are then labeled by an enzyme or a fluorescent dye.

Example 5

Detection of Ergosterol Using MIP for Ergosterol/Ergosterol-Dienophile Adduct

Molecularly imprinted polymers (MIPs) have been widely studied as recognition moieties that mimic the specific binding of antibodies and other biological entities to a target compound. Herein, the MIP technology is used for detecting ergosterol, while utilizing the ergosterol-dienophile adduct described herein.

In a representative example, a methodology for detecting ergosterol using the MIP technology according to the present embodiments is based on the Diels-Alder reaction between ergosterol and 4-(p-phenyl sulfonic acid)-[1,2,4]triazole-3,5-dione (TAD-PS, Compound 5), which produces the ergosterol-TAD-PS adduct Compound 6.

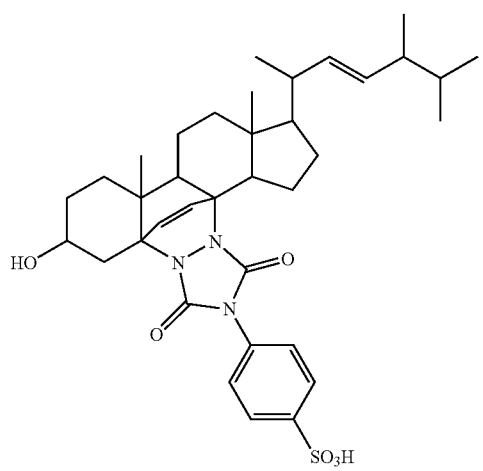

Compound 6

This exemplary methodology can be utilized in various assay principles, as follows.

In one example, MIP-covered microtiter plates are prepared by polymerizing a N-(2-aminoethyl)methacrylamide salt of a Diels-Alder adduct of ergosterol (e.g., Compound 6) in the presence of a 20-fold excess of ethylene glycol dimethacrylate (EGDMA), and optionally additional monomers, using known procedures for MIP formation, to thereby form a thin layer of the MIP-adduct complex on the flat bottoms of the microtiter plates. Extraction of the ergosterol adduct affords a MIP having pendant functional amine groups, designed to capture, for example, an adduct of ergosterol and a TAD-PS, via interaction of the amine groups with the sulfonic acid.

A labeled ergosterol-TAD adduct, such as, for example, Compound 4, or preferably, an ergosterol-TAD adduct in which the TAD substituted at position 4 by a fluorescent moiety (e.g., a bimane) which is turn is substituted by a e.g., $CO_2H$ or $SO_3H$, is then charged onto the MIP-covered plates.

Analysis is performed by extracting ergosterol from the tested sample, as described hereinabove, followed by reacting the ergosterol with TAD-PS (Compound 5) to thereby form the adduct 6.

Contacting Compound 6 with the MIP plates described hereinabove, charged with the labeled ergosterol-TAD adduct, results in the release of the labeled ergosterol-TAD adduct, which is detected and quantified using a detector of choice (e.g., a fluorescence or UV-VIS detector), to thereby determine the presence and level of ergosterol in the tested sample.

The above described pathway can optionally be effected by converting the ergostrol-TAD-PS adduct (Compound 6) to a sulfonyl chloride derivative thereof prior to contacting it with the MIP. Such a modification results in the formation of covalent interactions between the MIP and the analyte during the detection procedure and allows determination of the presence and level of ergosterol in the tested sample, as well as the fungal source of the ergosterol.

The above described pathway can be modified by similarly preparing MIPs with various pendant functional groups, which are selected suitable for complexing the desired ergosterol-dienophile adduct. Thus, various derivatives of the ergosterol-dienophile adduct can be used during the MIP formation, so as to produce the MIP of choice. Examples of such functional groups which are suitable to complex the sulfonic acid in an ergosterol-TAD-PS adduct include N,N'-diethyl(4-vinylphenyl)amidine (DEVPA) and cyclic-ethylene guanidine derivatives.

In another example, MIP-covered microtiter plates are prepared such that a MIP having pendant groups of the dienophile (e.g., TAD) is formed. Upon extraction of ergosterol from the tested sample, the extract is reacted with the MIP and an adduct with the TAD bound within the polymer binding sites is formed. The binding of ergosterol is detected by the displacement of a steroid similar to ergosterol but one which cannot react with TAD (e.g., cholesterol), which is covalently linked to a fluorescent dye. When the ergosterol from the test sample binds and reacts with the TAD inside the MIP, the fluorescently labeled steroid is displaced and gives a fluorescent signal, detected as described above.

Using MIP particles that bind ergosterol-TAD adducts, a lateral flow assay is constructed. In an exemplary assay, dye-colored MIP particles (which also contain magnetite) having an ergosterol-TAD adduct that contains an exposed azide group bound thereto are prepared. Upon contacting a test sample that contains ergosterol, ergosterol-TAD-azide adduct is formed. The resulting particles are placed at the bottom of a lateral flow device and are eluted upward. At the first line of the device, acetylene groups that are immobilized to the device at this line react, via "click chemistry" [e.g., H. C. Kolb and K. B. Sharpless, The Growing Impact of Click Chemistry on Drug Discovery, *Drug Discovery Today*, 8, 1128 (2003)], so as to bind the colored particles. This line indicates the presence of ergosterol in the sample. As the unbound particles elute further upwards to the second line they are bound by magnetic particles immobilized to the device at this second line. The presence of this line indicates that the device is working, i.e., that the eluent is carrying the particles upwards the device. Thus, a single line at the top indicates no ergosterol to be present; two lines indicate that ergosterol is present in the sample; a single line at the middle of the device or no line indicates that the device is not operating properly.

Example 6

Detection of Ergosterol Using Quartz Crystal Microbalance

The Quartz Crystal Microbalance (QCM) is an extremely sensitive mass sensor capable of measuring mass changes in the nano-gram range. QCMs are piezoelectric devices fabricated of a thin plate of quartz with electrodes affixed to each side of the plate. FIG. 6a presents a schematic view of a QCM detector.

Ergosterol detection is achieved by utilizing a QCM substrate coated with a compound that can (selectively) form a conjugate with ergosterol (also referred to as a special capturing material or SCM). Thus, for example, a TAD substituted by disulfide moiety is bound to the gold surface of the QCM detector. Changes in the frequency of the crystal, resulting from ergosterol attachment to the coated QCM are used as indicator for the presence of ergosterol. FIG. 6b schematically illustrates the detection process.

In an exemplary experiment, a disulfide derivative of TAD, Compound 7 (see, Scheme 2), was prepared and bound to the gold surface of a QCM device. Compound 7 is capable of forming a Diels-Alder adduct with two molequivalents of ergosterol, so as to obtain Compound 8, as illustrated in Scheme 2.

Scheme 2

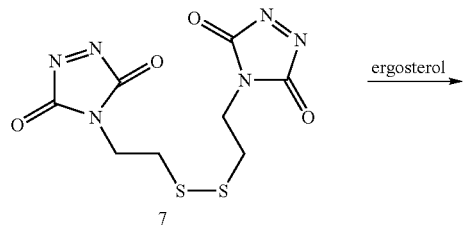

ergosterol →

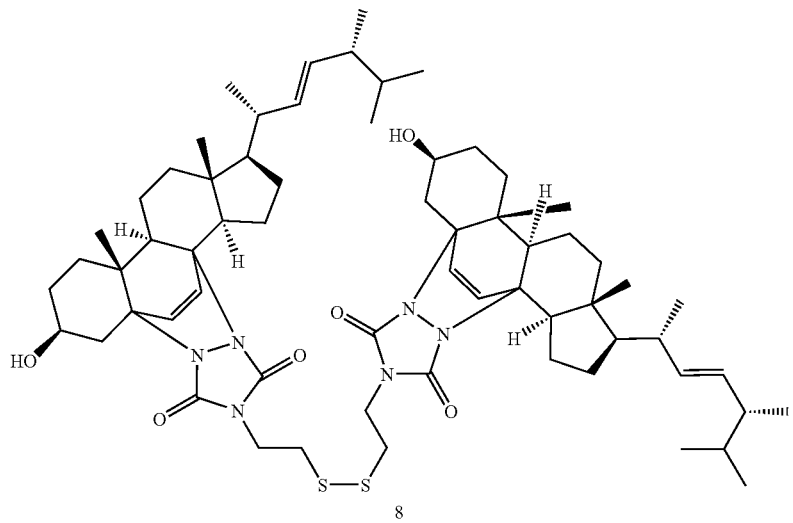

Preparation of a Disulfide Derivative of TAD (Compound 7)

Preparation of bis[4-ethyl-(1,2,4)triazole]disulfide

Bis[4-ethyl-(1,2,4)triazole]disulfide was prepared as illustrated in Scheme 3 below.

Scheme 3

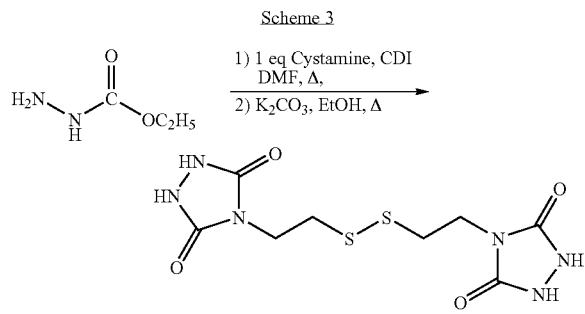

Cystamine dihydrochloride salt (1 equivalent) and diethyl carbazate (2 equivalents) were dissolved in dry DFM. Carbon diimidazole (CDI, 2 equivalents) was added to the solution, followed by triethyl amine (2 equivalents) and the resulting mixture was stirred overnight at room temperature and thereafter refluxed for additional 2 hours. The solvent was then removed and the residue was suspended in ethanol. Potassium carbonate (4 equivalents) was added and the resulting mixture was refluxed overnight. The solvent was thereafter removed, and the residue was dissolved in water. Concentrated HCl was added to the aqueous solution to adjust the pH to 4. The obtained white precipitate was filtered, washed consecutively with water, ethyl acetate and hexane, and dried at 60° C. The product was obtained in 50% yield.

m.p.=170° C.

Elemental analysis: Calc. for $C_8H_{12}N_6O_4S_2$: C, 29.99; H, 3.78; N, 26.23; S, 20.02. Found: C, 30.18; H, 3.97; N, 25.93; S; 19.54.

Preparation of bis[4-ethyl-(1,2,4)triazol-3,5-dione]disulfide

Bis[4-ethyl-(1,2,4)triazole]disulfide (100 mg) was oxidized to the bis[4-ethyl-(1,2,4)triazol-3,5-dione]disulfide according to the method described in Zolfigol et al. [Tetrahedron, 2001. 57: p. 8381-8384]. In brief, sulfuric silica gel (1.5 grams) and wet silica (1 gram, 1:1 w/w) were added to dry $CH_2Cl_2$ (20 ml) and $NaNO_2$ (0.3 gram) was added thereto in three portions over 1 hour. The resulting mixture was stirred for two hours at room temperature, so as to obtain a red-colored solution containing Compound 7.

Preparation of a QCM Substrate Coated with Compound 7

The red-colored $CH_2Cl_2$ solution obtained as described above was divided into several glass vials (2 ml per vial) and QCM plates were immersed in the vials for 1 hour. The crystals were thereafter washed with $CH_2Cl_2$ and their fundamental frequencies were recorded.

Detection of Ergosterol:

Four QCM substrates were used. One substrate was used as a control and the other three substrates (denoted QCM 45, 46 and 47) were coated by Compound 7, as described hereinabove.

The QCM plates were immersed in $CH_2Cl_2$ solutions (20 mM, 2 ml) containing either ergosterol (QCM 46 and 47) or cholesterol (QCM 45) and the crystal frequencies were measured. QCM 45 was further immersed in an ergosterol solution and its frequency was measured again. The obtained data is presented in Table 1 below.

TABLE 1

| QCM modified with SCM | QCM 46 incubated in Ergosterol solution | QCM 47 Incubated in Ergosterol solution | QCM 45* Incubated in Cholesterol solution | QCM 45* Incubated in Cholesterol solution followed by incubation in ergosterol |
|---|---|---|---|---|
| QCM frequency | 5971044.5 Hz | 5966783.5 Hz | 5970173.0 Hz | |
| Change in QCM frequency | 48.5 Hz | 44 Hz | 2 Hz | 16 Hz |

The obtained data clearly demonstrate the selective binding of ergosterol to a TAD-modified QCM substrate and indicate that such QCM substrates can be efficiently utilized for detecting ergosterol.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of determining a presence of an ergosterol-containing organism in a substrate, by detecting a presence of ergosterol in the substrate, the method comprising:

isolating a sterol-containing portion of the substrate, by subjecting the substrate to extraction, using an organic hydrophobic solvent;

contacting said sterol-containing portion with a compound capable of selectively forming a conjugate with ergosterol in said sterol-containing portion of the substrate, said compound being a [1,2,4]-triazole-3,5-dione (TAD); and determining a presence of said conjugate by a spectroscopic assay, said presence of said conjugate being indicative for the presence of ergosterol and thereby indicative for the presence of an ergosterol-containing organism in the substrate.

2. The method of claim 1, wherein said compound comprises a detectable moiety.

3. The method of claim 1, wherein said spectroscopic assay is based on spectral properties exerted by said conjugate when subjected to an external energy.

4. The method of claim 1, wherein said ergosterol-containing organism is a fungus.

5. The method of claim 1, wherein said substrate is a bodily substrate selected from the group consisting of an organ, a tissue and a cell.

6. The method of claim 5, being for detecting a fungal infection in a subject comprising said bodily substrate.

7. The method of claim 6, wherein said substrate is a blood sample.

8. The method of claim 1, wherein said substrate is selected from the group consisting of a construction, a storage container, a soil, an agricultural crop, a horticultural crop, an agricultural product, a food product, a cosmetic product, a paint, a lumber and a building material.

* * * * *